US011297868B2

(12) United States Patent
Shemesh et al.

(10) Patent No.: US 11,297,868 B2
(45) Date of Patent: *Apr. 12, 2022

(54) METHOD OF GENERATING BACTERIAL COMPOSITIONS

(71) Applicants: The State of Israel, Ministry of Agriculture & Rural Development, Agricultural Research Organization (ARO) (Volcani Center), Rishon-LeZion (IL); Yissum Research Development Company of the Hebrew University of Jerusalem Ltd., Jerusalem (IL)

(72) Inventors: Moshe Shemesh, Modiln (IL); Ram Reifen, Rehovot (IL)

(73) Assignees: The State of Israel, Ministry of Agriculture & Rural Development, Agricultural Research Organization (ARO) (Volcani Center), Rishon-LeZion (IL); Yissum Research Development Company of the Hebrew University of Jerusalem Ltd., Jerusalem (IL)

(*) Notice: Subject to any disclaimer, the term of this patent is extended or adjusted under 35 U.S.C. 154(b) by 50 days.

This patent is subject to a terminal disclaimer.

(21) Appl. No.: 16/304,697

(22) PCT Filed: May 29, 2017

(86) PCT No.: PCT/IL2017/050603
§ 371 (c)(1),
(2) Date: Nov. 27, 2018

(87) PCT Pub. No.: WO2017/208237
PCT Pub. Date: Dec. 7, 2017

(65) Prior Publication Data
US 2019/0216124 A1 Jul. 18, 2019

Related U.S. Application Data

(60) Provisional application No. 62/342,975, filed on May 29, 2016.

(51) Int. Cl.
| | | |
|---|---|---|
| A23L 33/135 | (2016.01) | |
| A61K 35/742 | (2015.01) | |
| A61K 35/747 | (2015.01) | |
| C12N 1/20 | (2006.01) | |
| C12P 39/00 | (2006.01) | |
| C12R 1/25 | (2006.01) | |
| C12R 1/125 | (2006.01) | |

(52) U.S. Cl.
CPC .......... *A23L 33/135* (2016.08); *A61K 35/742* (2013.01); *A61K 35/747* (2013.01); *C12N 1/20* (2013.01); *C12N 1/205* (2021.05); *C12P 39/00* (2013.01); *C12R 2001/125* (2021.05); *C12R 2001/25* (2021.05)

(58) Field of Classification Search
CPC .......... C12N 1/20; A23L 33/135; C12P 39/00; C12R 1/24; C12R 1/25
See application file for complete search history.

(56) References Cited

U.S. PATENT DOCUMENTS

| | | |
|---|---|---|
| 2010/0203581 A1 | 8/2010 | Morinaga et al. |
| 2017/0020178 A1 | 1/2017 | Rubin |
| 2020/0190463 A1 | 6/2020 | Shemesh |

FOREIGN PATENT DOCUMENTS

| | | |
|---|---|---|
| CN | 103911323 | 7/2004 |
| CN | 103952336 | 7/2014 |
| CN | 104789508 | 7/2015 |
| CN | 107734972 | 2/2018 |
| WO | WO 2005/019417 | 3/2005 |
| WO | WO 2011/031020 | 3/2011 |
| WO | WO 2015/134808 | 9/2015 |
| WO | WO 2016/181228 | 11/2016 |
| WO | WO 2017/203440 | 11/2017 |
| WO | WO 2017/208237 | 12/2017 |
| WO | WO 2018/220630 | 12/2018 |

OTHER PUBLICATIONS

Abe et al. "Yeasts and Lactic Acid Bacteria Mixed-Specie Biofilm Formation is a Promising Cell Immobilization Technology for Ethanol Fermentation" Appl Biochem Biotechnol (2013) 171:72-79 (Year: 2013).*

Deepika et al. "A Study on Bioelectricity Production by the Synergistic Action of Bacillus Tequilensis DMR-5 and Pseudomonas Aeruginosa DMR-3 Isolated From Rumen Fluid" American Journal of Environmental Science 9 (5): 424-430, 2013 (Year: 2013).*

DSMZ "1241. Starch—Mineral Salt—AGAR (STMS) + 15% NaCI" and "84. Rolled Oats Mineral Medium" 2 pages (Year: 2010).*

Thein et al. "Effect of oral bacteria on growth and survival of Candida albicans biofilms" Archives of Oral Biology (2006) 51, 672-680 (Year: 2006).*

Yahav et al. "Encapsulation of beneficial probiotic bacteria in extracellular matrix from biofilm-forming Bacillus subtilis" Artificial Cells, Nanomedicine, and Biotechnology 2018, vol. 46, No. S2, S974-S982 (Year: 2018).*

International Preliminary Report on Patentability dated Dec. 13, 2018 From the International Bureau of WIPO Re. Application No. PCT/IE2017/050603. (9 Pages).

(Continued)

*Primary Examiner* — Thane Underdahl

(57) ABSTRACT

A method of preparing a bacterial composition is disclosed. The method comprises:
(a) in vitro co-culturing beneficial bacteria with biofilm-producing bacteria in a growth substrate under conditions that generate a biofilm which comprises the beneficial bacteria and the non-pathogenic bacteria; and
(b) isolating the biofilm from the growth substrate.

21 Claims, 20 Drawing Sheets
(16 of 20 Drawing Sheet(s) Filed in Color)

(56) References Cited

OTHER PUBLICATIONS

International Search Report and the Written Opinion dated Sep. 6, 2018 From the International Searching Authority Re. Application No. PCT/IL2018/050588. (12 Pages).
International Search Report and the Written Opinion dated Jul. 18, 2017 From the International Searching Authority Re. Application No. PCT/IL2017/050603. (12 Pages).
Bhat et al. "Bacillus Subtilis Natto: A Non-Toxic Source of Poly-Gamma-Glutamic Acid That Could Be Used as a Cryoprotectant for Probiotic Bacteria", AMB Express, 3(36): 1-9, Published Online Jul. 5, 2013.
Chang "Nuclear Waste Bioremediation", Submitted as Coursework for PH241, Stanford University, CA, USA, Winter 2016, 5 P., Mar. 11, 2016.
Dombrowski et al. "Scientists Want to Use Bacteria to Clean Up Oil Spills—and It Could Actually Work", The Conversation, 5 P., Jun. 23, 2016.
Graham et al. "Nano and Microscale Topographies for the Prevention of Bacterial Surface Fouling", Coatings, 4(1): 37-59, Jan. 17, 2014.
Gupta et al. "Bacterial Exopolysaccharide Mediated Heavy Metal Removal: A Review on Biosynthesis, Mechanism and Remediation Strategies", Biotechnology Reports, 13: 58-71, Available Online Dec. 23, 2016.
Hosoi et al. "Improved Growth and Viability of Lactobacilli in the Presence of Bacillus Subtilis (Natto), Catalase, or Subtilisin", Canadian Journal of Microbiology, 46(10): 892-897, Published Online Sep. 18, 2000.
Lebeer et al. "Impact of Environmental and Genetic Factors on Biofilm Formation by the Probiotic Strain Lactobacillus Rhamnosus GG", Applied and Environmental Microbiology, 73(21): 6768-6775, Published Online Sep. 7, 2007. p. 6768, First Para, p. 6770, Right Col., 2nd Para—p. 6772, Right Col., First Para, p. 6768, 1st Para.
Salas-Jara et al. "Biofilm Forming Lactobacillus: New Challenges for the Development of Probiotics", Microorganisms, 4(3): 35-1-35-14, Sep. 20, 2016.
Shemesh et al. "A Combination of Glycerol and Manganese Promotes Biofilm Formation in Bacillus Subtilis Via the Histidine Kinase KinD Signaling", Journal of Bacteriology, 195(12): 2747-2754, Published Online Apr. 5, 2013. Abstract, p. 2748, Right Col., Last Para, p. 2752, Right Col., First Full Para—p. 2753, Right Col., 1st Para, Figs.6, 7.
Van der Veen et al. "Mixed Species Biofilms of Listeria Monocytogenes and Lactobacillus Plantarum Show Enhanced Resistance to Benzalkonium Chloride and Peracetic Acid", International Journal of Food Microbiology, 144(3): 421-431, Oct. 29, 2010. Abstract, p. 422, Left Col., Last Para—p. 423, Left Col. 3rd Para, p. 429, Left Col., 3rd Para—Right Col., 1st Para, Table I With Refeence Herein, Figs.1-3.
Zhai et al. "Protective Effects of Lactobacillus Plantarum CCFM8610 Against Acute Cadmium Toxicity in Mice", Applied and Environmental Microbiology, 79(5): 1508-1515, Published Online Dec. 21, 2012. Abstract, p. 1509, Left Col., 2nd Full Para.
Zhandalgarova et al. "Probiotics of New Generation on the Basis of the Genera Bacillus, Bifidobacterium and Lactobacillus in the Composition of the Starting Feed as Grwoth Promoters Sturgeon Fish", World Aquaculture Society Meetings, World Aquaculture 2015—Meeting Abstract, 2 P., May 31, 2015.
International Preliminary Report on Patentability dated Dec. 12, 2019 From the International Bureau of WIPO Re. Application No. PCT/IL2018/050588. (9 Pages).
Supplementary European Search Report and the European Search Opinion dated Dec. 10, 2019 From the European Patent Office Re. Application No. 17806027.3. (8 Pages).
Fall et al. "A Simple Method to Isolate Biofilm-Forming Bacillus Subtilis and Related Species From Plant Roots", Systematic and Applied Microbiology, XP004957510, 27(3): 372-379, Jan. 2004.
Fernandez Ramirez et al. "Characterisation of Biofilms Formed by Lactobacillus Plantarum WCFS1 and Food Spoilage Isolates", International Journal of Food Microbiology, XP029187994, 207: 23-29, Available Online Apr. 24, 2015.
Jalilsood et al. "Inhibition of Pathogenic and Spoilage Bacteria by A Novel Biofilm-Forming Lactobacillus Isolate: A Potential Host for the Expression of Heterologous Proteins", Microbial Cell Factories, XP021226445, 14(1): 96-1-9614, Published Online Jul. 7, 2015.
Kimelman et al. "Probiotic Bifunctionality of Bacillus Subtilis—Rescuing Lactic Acid Bacteria From Desiccation and Antagonizing Pathogenic *Staphylococcus aureus*", Microorganisms, XP055647825, 7(10): 407-1-407-16, Published Online Sep. 29, 2019.
Restriction Official Action dated Oct. 7, 2021 from US Patent and Trademark Office Re. U.S. Appl. No. 16/618,137. (7 pages).
Zhou et al. "Virulence Regulator PrfA is Essential for Biofilm formation in Listeria Monocytogenes but not in Listeria Innocua", Current Microbiology, 63:186-192, 2011.
Examination Report Under Sections 12 & 13 of the Patents Act, 1970 and the Patents Rules, 2003 dated Sep. 7, 2021 From the Government of India, Intellectual Property India, Patents, Designs, Trade Marks, Geographical Indications, The Patent Office Re. Application No. 201827047319. (2 Pages).
Yan et al. "Genome-Wide Investigation of Biofilm Formation in Bacillus Cereus", Applied and Environmental Microbiology, 83(13): e00561-17-1-e00561-17-18, Published Online Apr. 21, 2017.
Supplementary European Search Report and the European Search Opinion dated Mar. 1, 2021 From the European Patent Office Re. Application No. 18810460.8. (13 Pages).
Calasso et al. "Effects of the Peptide Pheromone Plantaricin A and Cocultivation with Lactobacillus sanfranciscensis DPPMA174 on the Exoproteome and the Adhesion Capacity of Lactobacillus Plantarum DC400", Applied and Environmental Microbiology, XP055769378, 79(8):2657-2669, Apr. 1, 2013.
Cheow et al. "Biofilm-Like Lactobacillus rhamnosus Probiotics Encapsulated in Alginate and Carrageenan Microcapsules Exhibiting Enhanced Thermotolerance and Freeze-Drying Resistance", Biomacromolecules, XP55422567A, 14(9):3214-3222, Aug. 16, 2013.
Notification of Office Action and Search Report dated Nov. 3, 2021 From the State Intellectual Property Office of the People's Republic of China Re. Application No. 201780046868.7 and Its Translation of Office Action Into English. (5 Pages).

\* cited by examiner

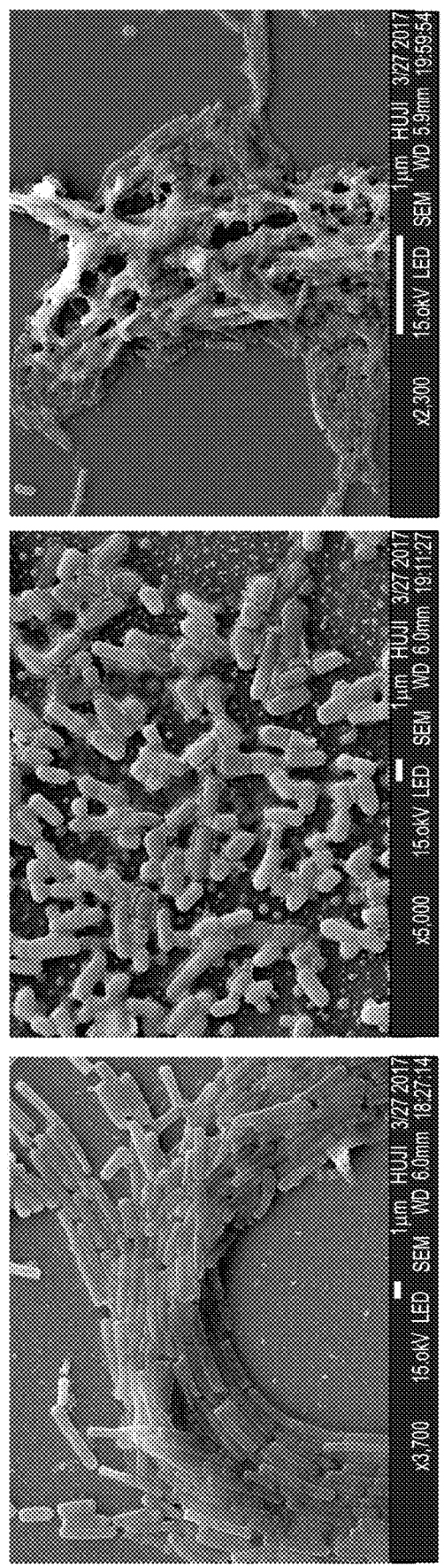

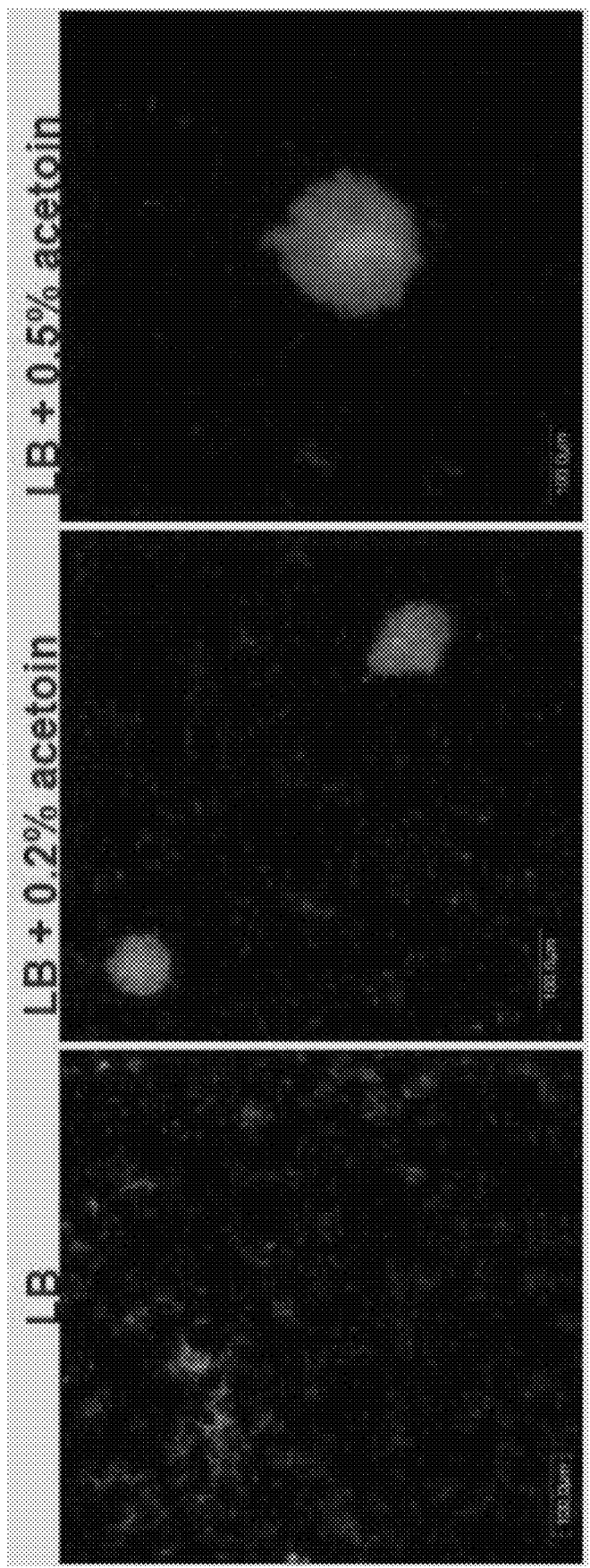

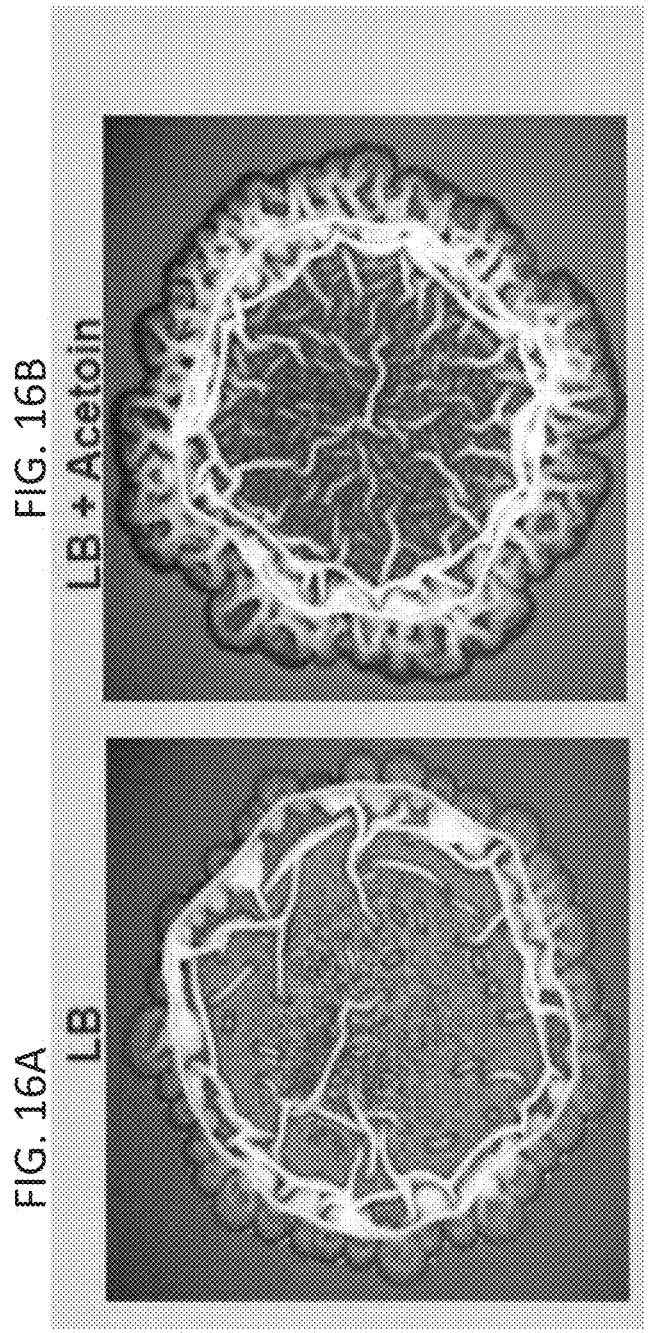

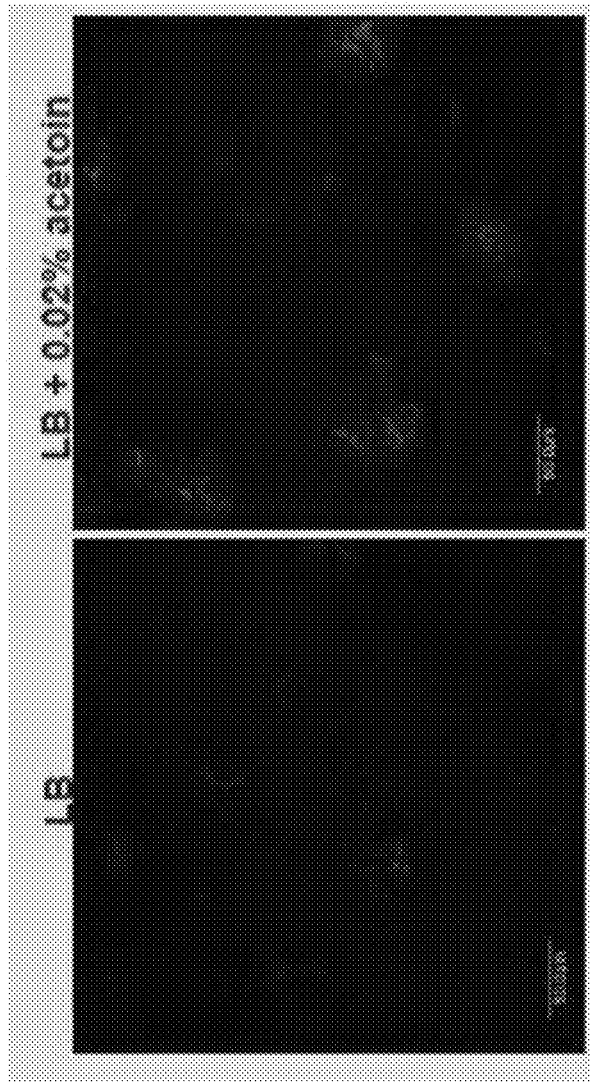
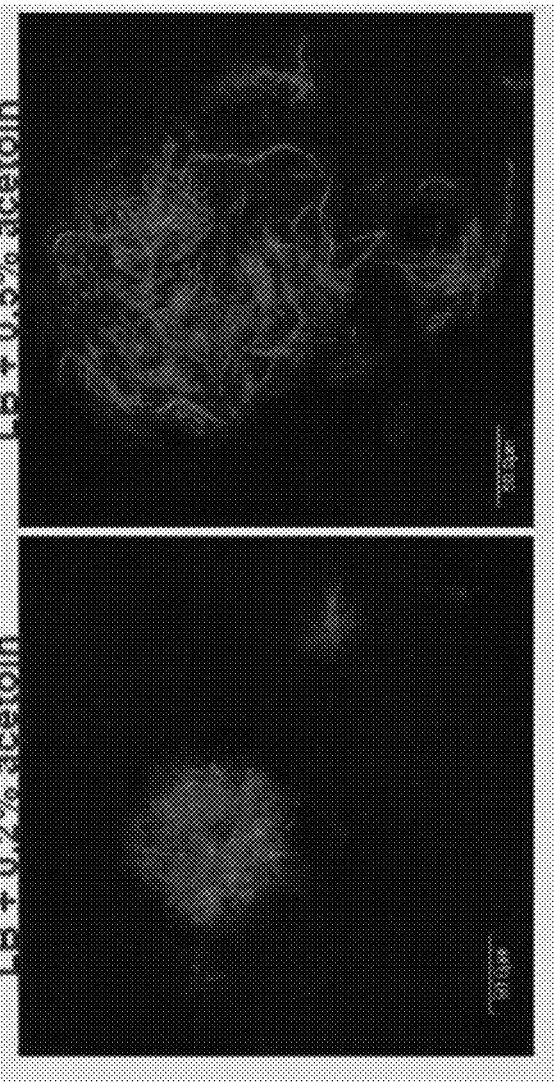
FIG. 17A  FIG. 17B  FIG. 17C  FIG. 17D

METHOD OF GENERATING BACTERIAL COMPOSITIONS

RELATED APPLICATIONS

This application is a National Phase of PCT Patent Application No. PCT/IL2017/050603 having International filing date of May 29, 2017, which claims the benefit of priority under 35 USC § 119(e) of U.S. Provisional Patent Application No. 62/342,975 filed on May 29, 2016. The contents of the above applications are all incorporated by reference as if fully set forth herein in their entirety.

FIELD AND BACKGROUND OF THE INVENTION

The present invention, in some embodiments thereof, relates to methods of generating bacterial compositions, more particularly, but not exclusively, to probiotic compositions, those beneficial to the environment and those used in industry.

Living microbial cells which are administered in adequate amounts, confer a beneficial physiological effect on the host, are known as "probiotics". Studies have shown therapeutic effects that probiotic bacteria can provide to the host in maintaining a healthy gut and controlling several types of gastrointestinal infections. Due to their perceived health benefits, probiotic bacteria have been increasingly incorporated into a variety of food and drink products during the last few decades. Some of the most common types of microorganisms used as probiotics are the lactic acid bacteria (LAB), which mainly belong to the genera *Lactobacillus* and *Bifidobacterium*. Both these genera are dominant inhabitants in the human intestine and have a long history of safe use and are considered as GRAS (generally recognized as safe). To assure their beneficial effects in the body, these organisms must survive during food processing, storage and the passage through the upper gastrointestinal tract (GIT) and arrive alive to their site of action. However, previous studies have shown low survival level of probiotic bacteria in the final food product and a considerable loss in their viability to high acidic conditions of the stomach and high bile concentration in the small intestine. In addition, probiotics are usually available as dry bacterial powders prepared mainly by freeze drying which has been established as a procedure that may cause fatal injury to cells. Therefore, there is a need to develop novel technologies aimed to improve the survival of health-promoting bacteria during food production, as well as through the storage and ingestion processes in order to maintain delivery of probiotics to humans.

In most natural ecosystems, bacteria prefer to grow in complex community of multicellular cells called biofilm and not as free-living (planktonic) cells. Biofilm mode of growth is preferable also for bacteria that inhabit the intestinal tract. Cells in a biofilm are bound together by an extracellular matrix that mainly consists of polysaccharides and other macromolecules such as proteins, DNA, lipids and nucleic acids, which are produced by the cells themselves. Interactions between the species embedded in the biofilm and their environment result in the formation of a complex structure, capable of resisting to environmental stress and exposure to antimicrobial agents. Thus, biofilm formation represents a strategy for persistence under unfavorable conditions in diverse environments.

One of the mostly studied biofilm formers is *Bacillus subtilis*, a spore-forming non-pathogenic bacterium, which is characterized by its ability to produce a robust biofilm. *Bacillus* species, principally *B. subtilis*, have gained recent interest as probiotic microorganism since they were shown to positively effect on host health status mainly by keeping a favorable balance of microflora in the gastrointestinal tract. Since *B. subtilis* spores are capable of surviving extreme pH conditions and low oxygen, high numbers of dormant but viable microbes may reach the lower intestine which may induce some beneficial effects through secretion of active substances. Furthermore, it was found that *B. subtilis* cells enhance growth and viability of lactobacilli spp., possibly through the production of catalase and subtilisin (Hosoi, Ametani, Kiuchi, & Kaminogawa, 2000). It has also been reported that γ-polyglutamic acid produced by *B. subtilis* as part of an extracellular matrix could be used to improve the survival of probiotic bacteria during freeze drying (A. R. Bhat et al., 2013) and during storage (A. R. Bhat et al., 2015). Likewise, during simulated gastric juice which simulated the acidic conditions of the stomach (A. R. Bhat et al., 2015).

Additional background art includes US Application No. 20100203581 and Salas Jara et al., Microorganisms 2016, 4, 35; doi: 10.3390.

SUMMARY OF THE INVENTION

According to an aspect of the present invention there is provided a method of preparing a bacterial composition comprising:

(a) in vitro co-culturing beneficial bacteria with biofilm-producing bacteria in a growth substrate under conditions that generate a biofilm which comprises the beneficial bacteria and the non-pathogenic bacteria; and (b) isolating the biofilm from the growth substrate, thereby preparing the bacterial composition.

According to an aspect of the present invention there is provided a bacterial composition obtainable according to the methods described herein.

According to an aspect of the present invention there is provided a food/feed product comprising the bacterial composition described herein.

According to an aspect of the present invention there is provided a method of improving or maintaining the health of a subject comprising administering to the subject a therapeutically effective amount of the probiotic composition described herein, thereby improving or maintaining the health of the subject.

According to an aspect of the present invention there is provided a method of selecting an agent or culturing condition which is advantageous for preparing a bacterial composition, the method comprising co-culturing beneficial bacteria with biofilm-producing bacteria in a growth substrate in the presence of the agent or under the culturing condition, so as to generate a biofilm comprising the beneficial bacteria and the biofilm-producing bacteria, wherein a change in a property of the biofilm is indicative of the agent or culturing condition being advantageous for preparing the bacterial composition.

According to embodiments of the present invention the biofilm-producing bacteria are non-pathogenic bacteria.

According to embodiments of the present invention the biofilm-producing bacteria are of the *bacillus* genus.

According to embodiments of the present invention the biofilm-producing bacteria are of the *B. subtilis* species.

According to embodiments of the present invention the beneficial bacteria are probiotic bacteria.

According to embodiments of the present invention the beneficial bacteria are genetically modified to express a therapeutic polypeptide.

According to embodiments of the present invention the probiotic bacteria is of the lactobacillales order.

According to embodiments of the present invention the biofilm-producing bacteria are of the *B. subtilis* species.

According to embodiments of the present invention the probiotic bacteria are of the *L. plantarum* species.

According to embodiments of the present invention the beneficial bacteria are used in bioremediation.

According to embodiments of the present invention the biofilm-producing bacteria express genes of the KinD-Spo0A pathway.

According to embodiments of the present invention the growth substrate comprises a growth medium.

According to embodiments of the present invention the growth medium is selected from the group consisting of LB, LBGM, milk and MRS.

According to embodiments of the present invention the biofilm-producing bacteria are of the *bacillus* genus and the beneficial bacteria are of the lactobacillales order, the growth substrate is LBGM, milk or MRS.

According to embodiments of the present invention the growth substrate is MRS.

According to embodiments of the present invention the conditions comprise a pH of about 6.5-8.

According to embodiments of the present invention the conditions comprise a pH of 6.8-7.5.

According to embodiments of the present invention the growth substrate comprises acetoin.

According to embodiments of the present invention the method further comprises dehydrating the biofilm following the isolating.

According to embodiments of the present invention the beneficial bacteria comprises no more than 50 bacterial species.

According to embodiments of the present invention the biofilm-producing bacteria are a single species of biofilm-producing bacteria.

According to embodiments of the present invention, at least 50% of the bacteria in the composition are viable.

According to embodiments of the present invention the bacterial composition comprises no more than 50 bacterial species of beneficial bacteria.

According to embodiments of the present invention the bacterial composition comprises a single species of non-pathogenic bacteria.

According to embodiments of the present invention the bacterial composition is edible.

According to embodiments of the present invention the bacterial composition is a probiotic bacterial composition.

According to embodiments of the present invention the bacterial composition is formulated as a powder, a liquid or a tablet.

According to embodiments of the present invention the biofilm-producing bacteria are of the *bacillus* genus.

According to embodiments of the present invention the biofilm-producing bacteria are of the *B. subtilis* species.

According to embodiments of the present invention the beneficial bacteria are probiotic bacteria.

According to embodiments of the present invention the probiotic bacteria are of the lactobacillales order.

According to embodiments of the present invention the agent alters the pH of a medium of the system.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B:
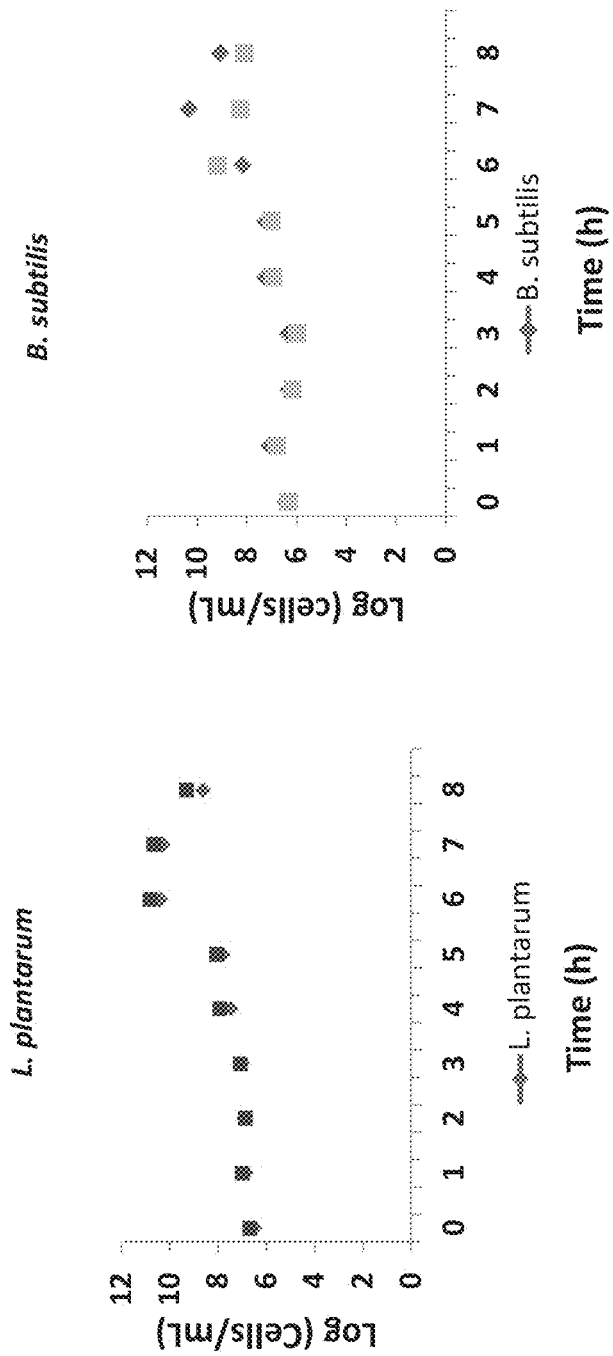

FIGS. 1A-B are graphs comparing *B. subtilis* and *L. plantarum* growth in co-culture. The co-culture generation had no effect on *L. plantarum* and *B. subtilis* growth (compared to their growth in pure culture), indicating that there are no antagonistic interactions between these bacteria.

Figure 2:
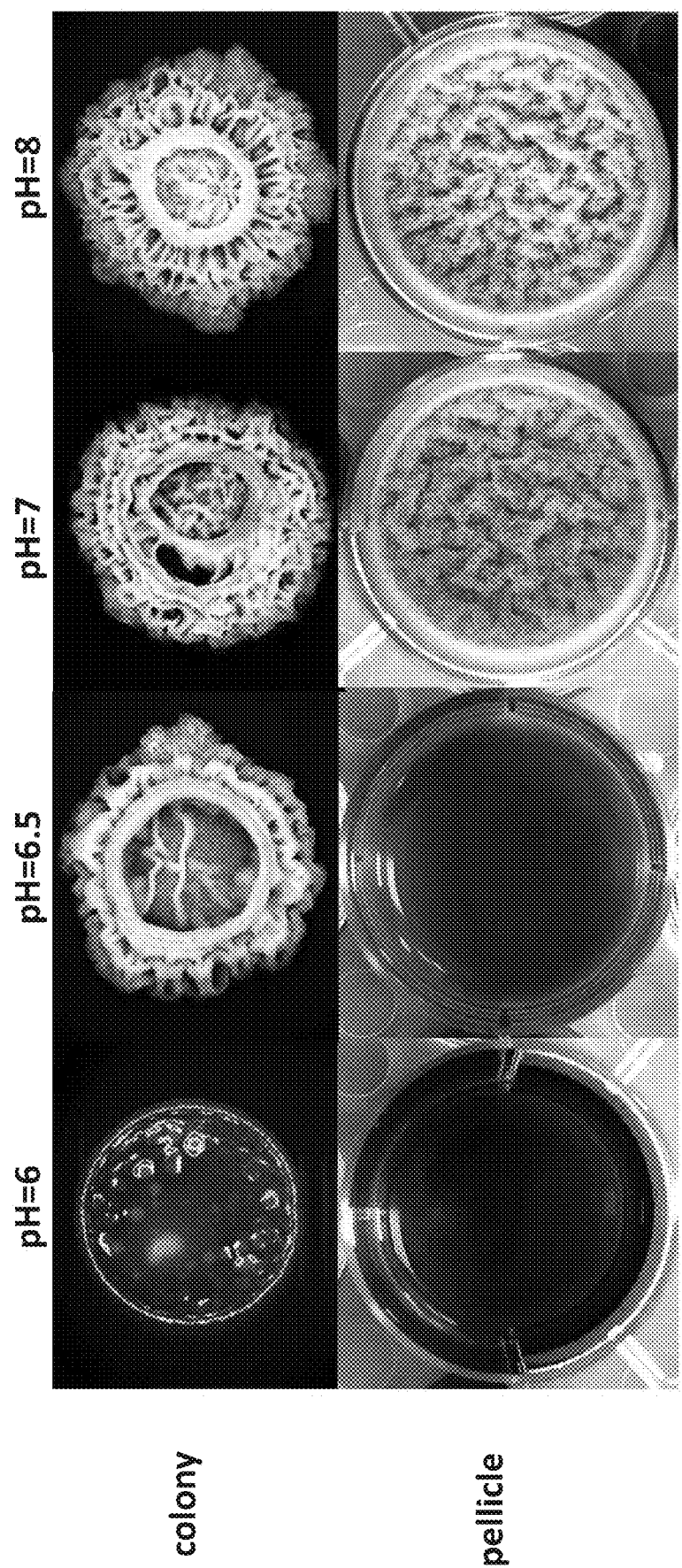

FIG. 2 are photographs illustrating that modified MRS medium triggers biofilm formation by *B. subtilis*. The effect of the pH modification of MRS on *B. subtilis* NCIB3610 biofilm formation was analyzed using stereoscopic microscope.

Figure 3:
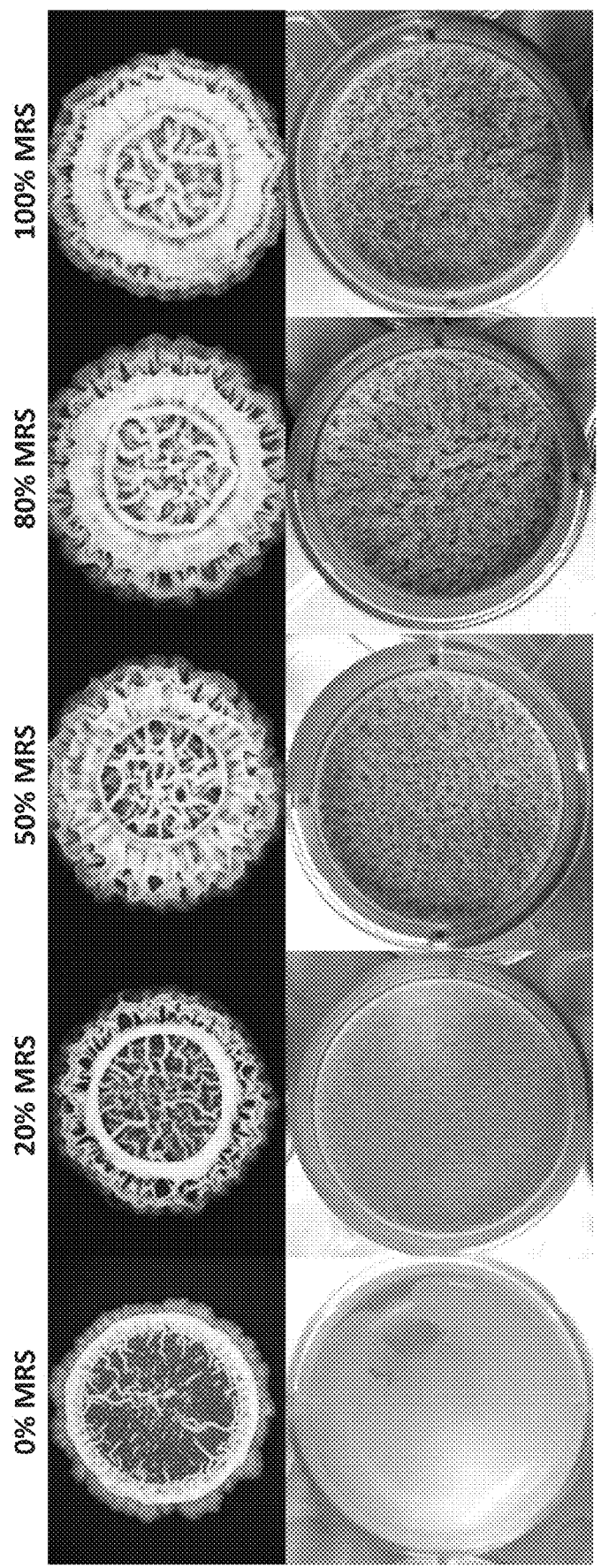

FIG. 3 are photographs illustrating that the combination of LB with MRS medium triggers biofilm development by *B. subtilis*. The effect of LB medium enriched with different concentrations of MRS (pH 7) on colony (top row) and pellicle (bottom row) biofilm formation.

Figures 4A, 4B:
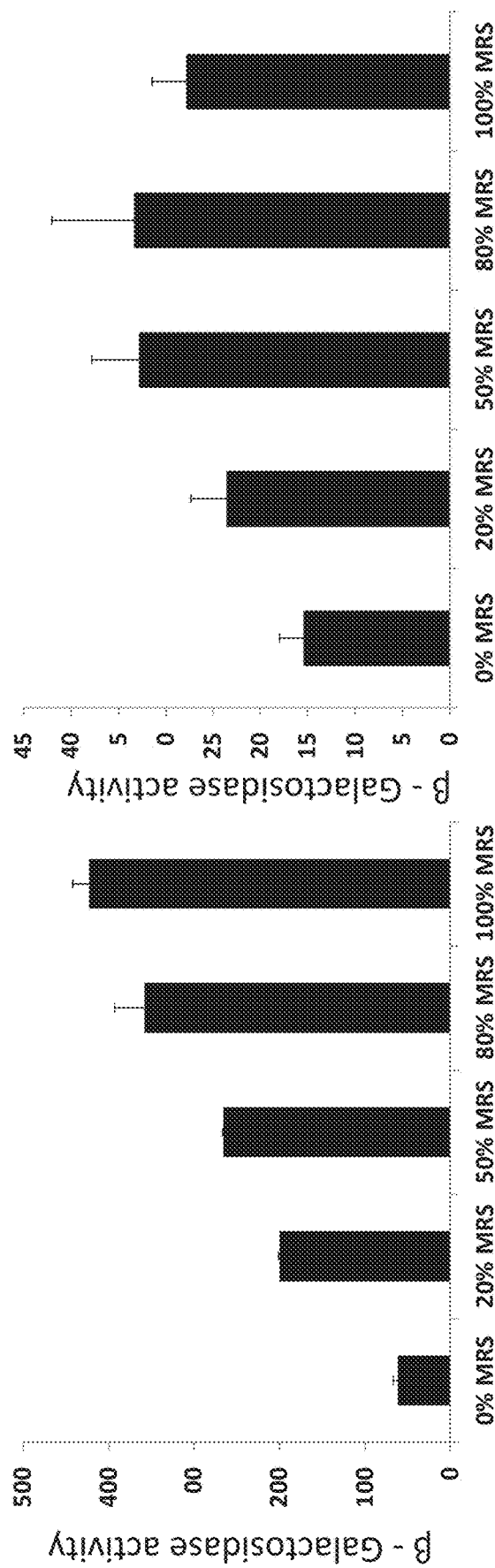

FIGS. 4A-B are graphs illustrating that the combination of LB with MRS medium triggers extracellular matrix production by *B. subtilis*. Increasing MRS concentration induces transcription of tapA-sipW-tasA (A) and epsA-O (B) operons.

Figure 5A:
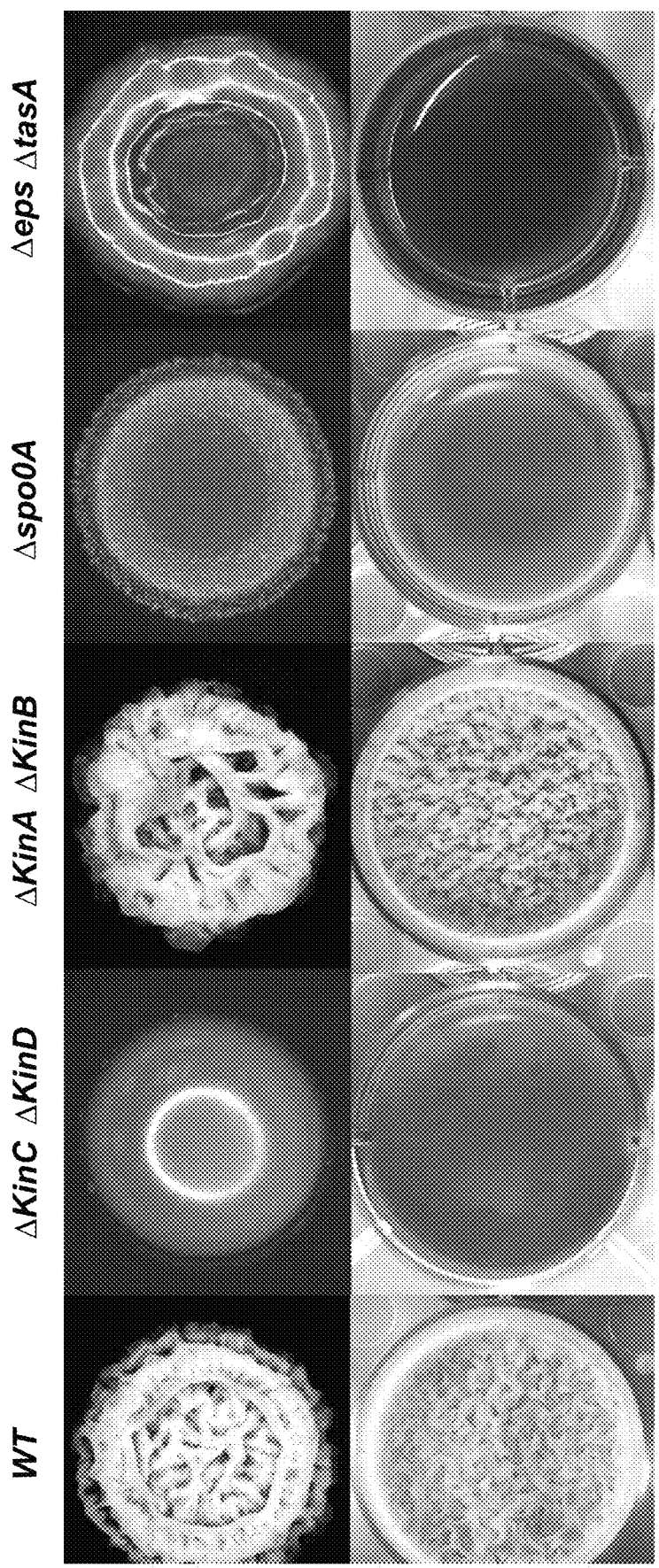

FIG. 5A are photographs illustrating that the biofilm stimulating effect of MRS is regulated by the matrix synthesis and biofilm forming signaling pathway previously described in *B. subtilis*. Colony development and pellicle formation on MRS (pH 7) by the wild type (WT) and various mutant strains were compared. The strains used here were as follows: wild type (NCIB3610), ΔkinCD (RL4577), ΔkinAB (RL4573), Δspo0A (RL4620), ΔepsΔtasA (RL4566), ΔabrB (YC668).

Figure 5B:
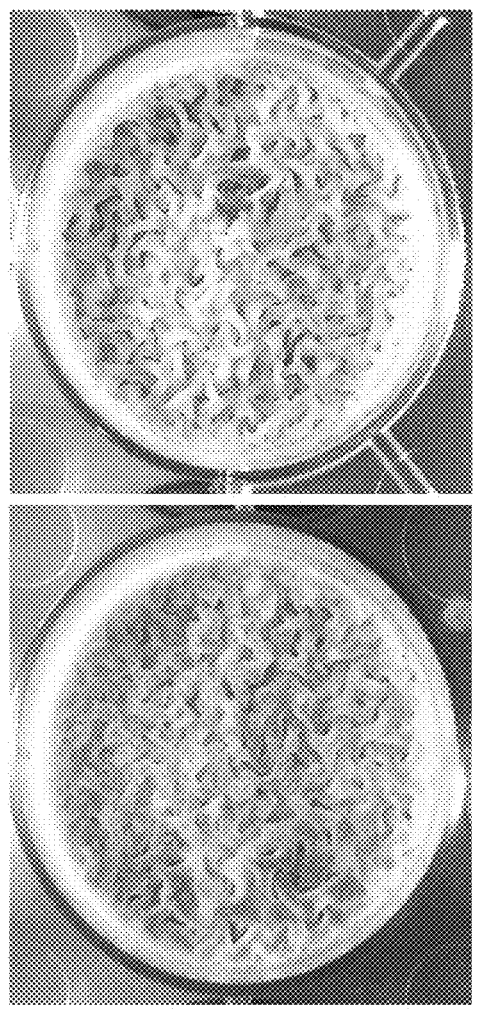

FIG. 5B are photographs illustrating that the effect of MRS in WT cells is comparable to the matrix overproducing mutant cells (ΔabrB) in *B. subtilis*.

Figure 6:
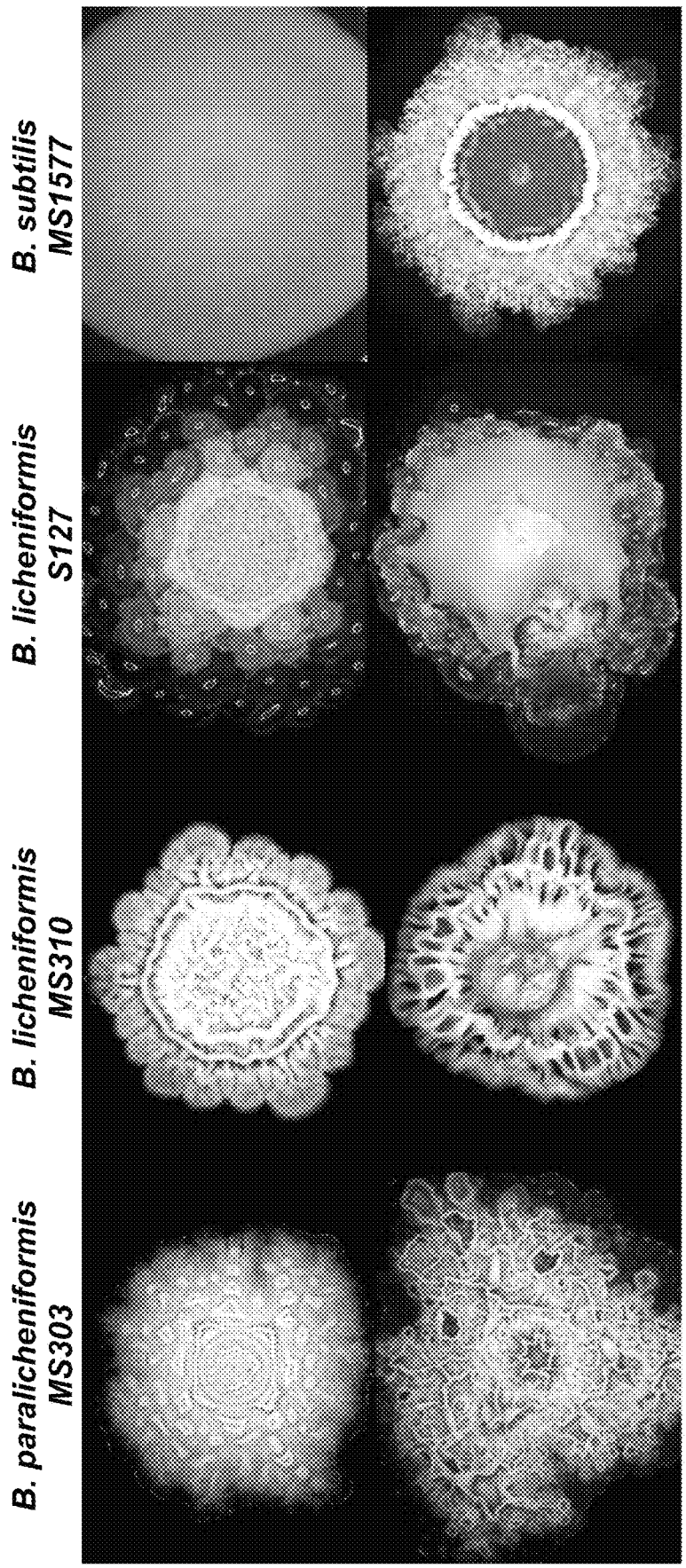

FIG. 6 are photographs illustrating that MRS induces colony biofilm formation in different *Bacillus* species. MRS (pH 7) medium strongly induced colony type biofilm formation of *B. paralicheniformis* MS303, *B. licheniformis* MS310, *B. licheniformis* S127, *B. subtilis* MS1577 and *B. cereus* 10987.

Figure 7:
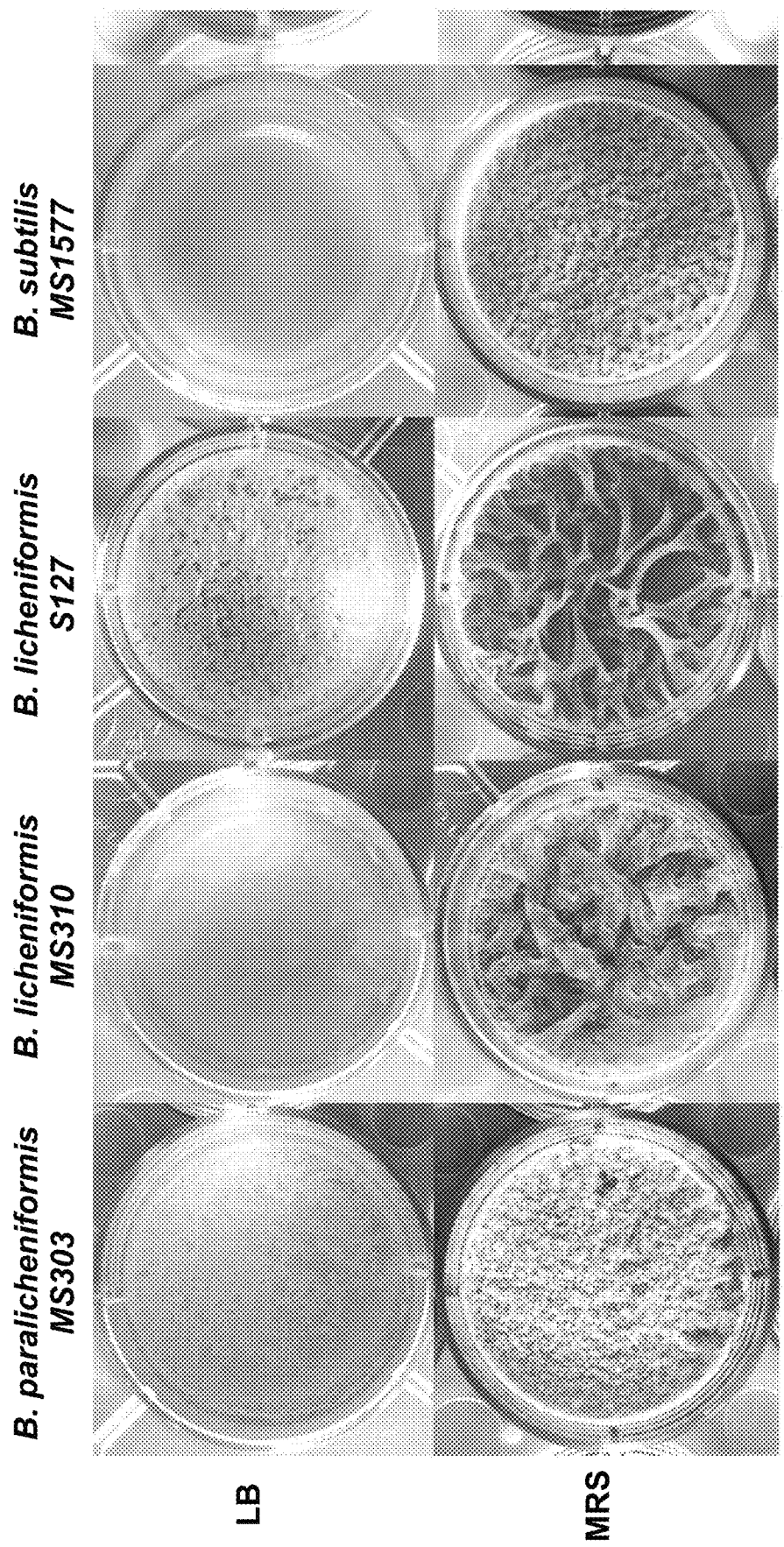

FIG. 7 are photographs illustrating that MRS induces pellicle formation in different *Bacillus* species. MRS (pH 7) medium strongly induced pellicle formation of *B. parali-* cheniformis MS303, *B. licheniformis* MS310, *B. licheniformis* S127, *B. subtilis* MS1577 and *B. cereus* 10987.

Figure 8A:
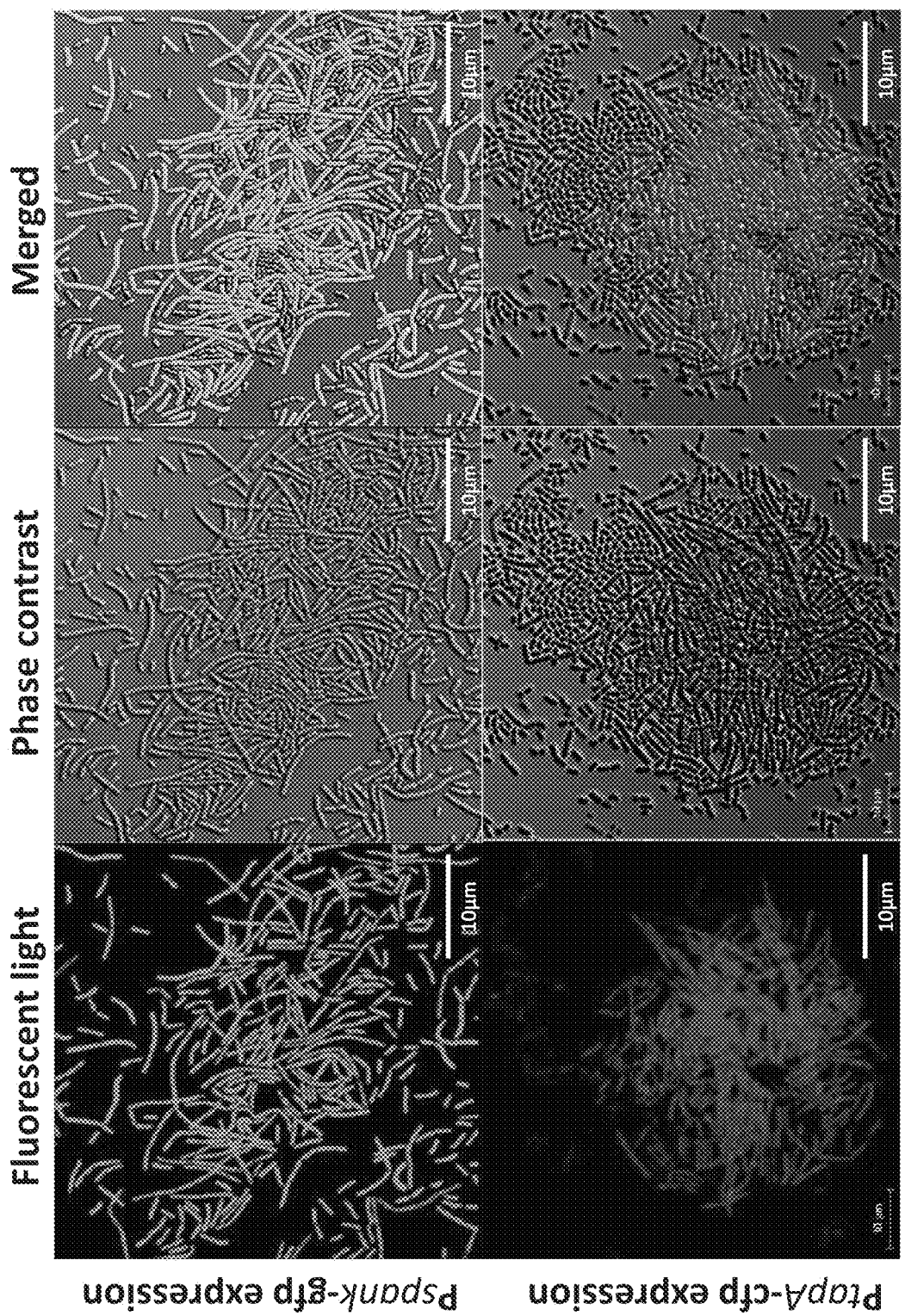
Figure 8B:
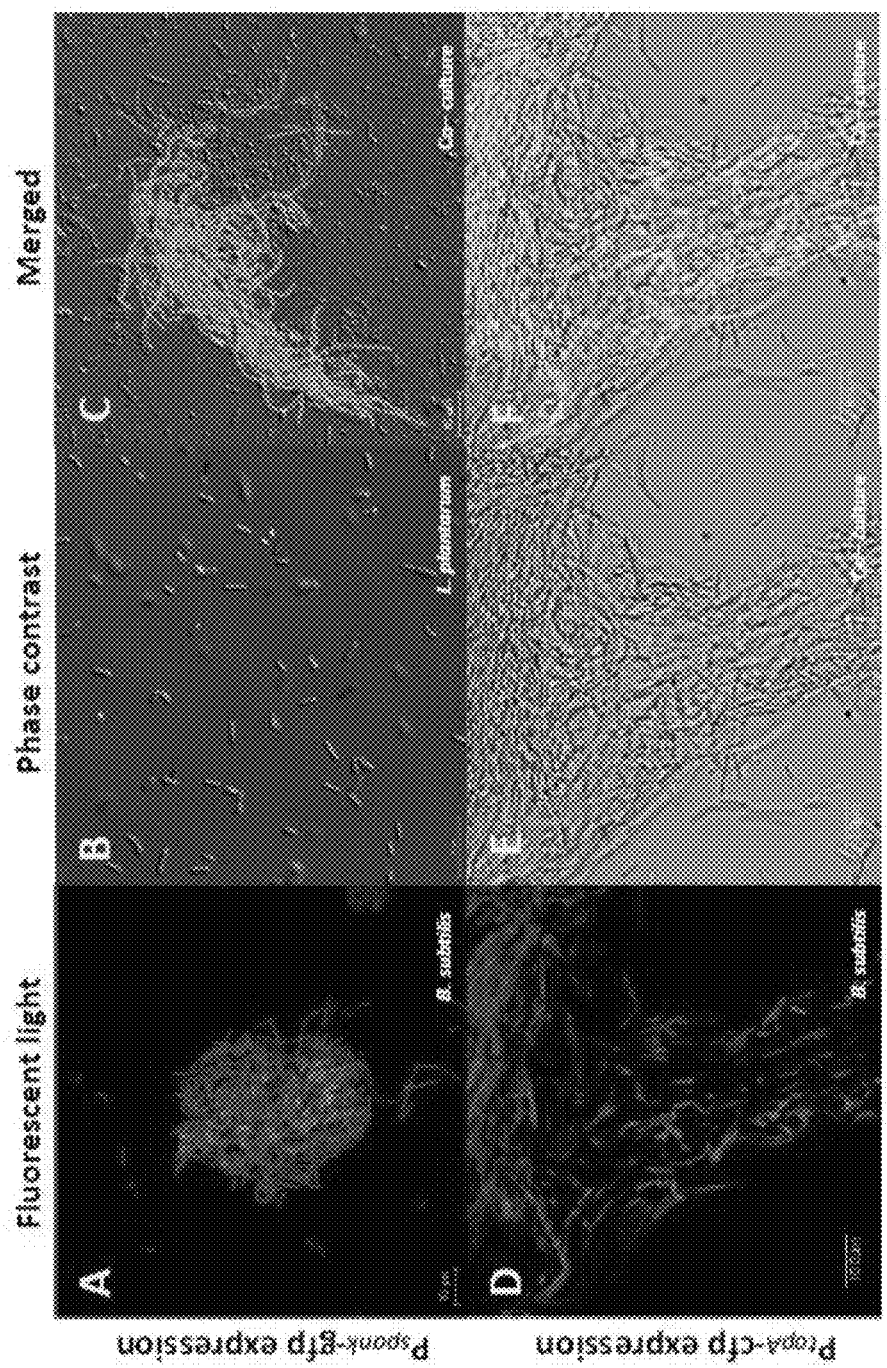

FIGS. 8A-B are images illustrating that *B. subtilis* produces extracellular matrix whilst forming a dual-species biofilm with *L. plantarum*. 8A. CLSM images of co-culture biofilm of *B. subtilis* and *L. plantarum* in MRS pH 7 at 37° C. and 50 rpm. From left to right: images made using fluorescent light, Nomarski differential interference contrast (DIC) and merged image. Top panel shows the expression of fluorescently tagged *B. subtilis* cells constitutively express GFP. Bottom panel shows expression of matrix producing *B. subtilis* cells express CFP under the control of tapA promoter. In all images *L. plantarum* cells are not stained. 8B. CLSM images of co-culture biofilm of *B. subtilis* and *L. plantarum* in LBGM medium. From left to right: images made using fluorescent light, Nomarski differential interference contrast (DIC) and merged image. Top panel shows the expression of fluorescently tagged *B. subtilis* cells constitutively express GFP. Bottom panel shows expression of matrix producing *B. subtilis* cells express CFP under the control of tapA promoter. In all images *L. plantarum* cells are not stained.

FIGS. 9A-C are SEM images of (A) *B. subtilis* cells, (B) *L. plantarum* cells and (C) dual species biofilm composed of *B. subtilis* and *L. plantarum*.

Figure 10A:
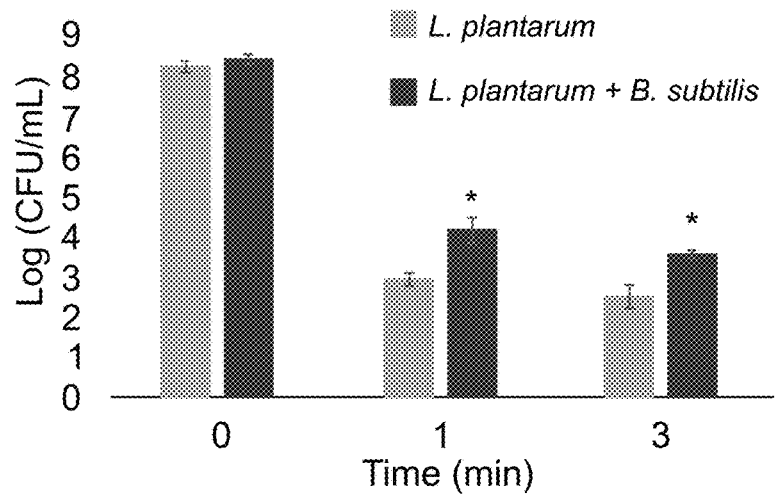
Figure 10B:
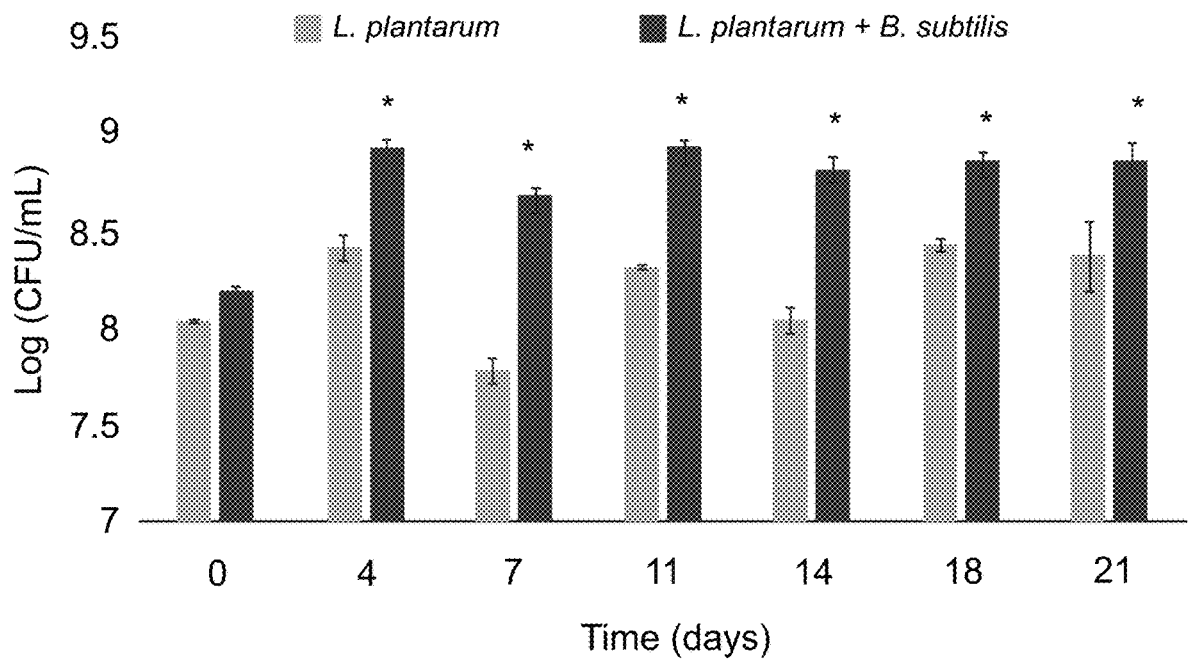
Figure 11A:
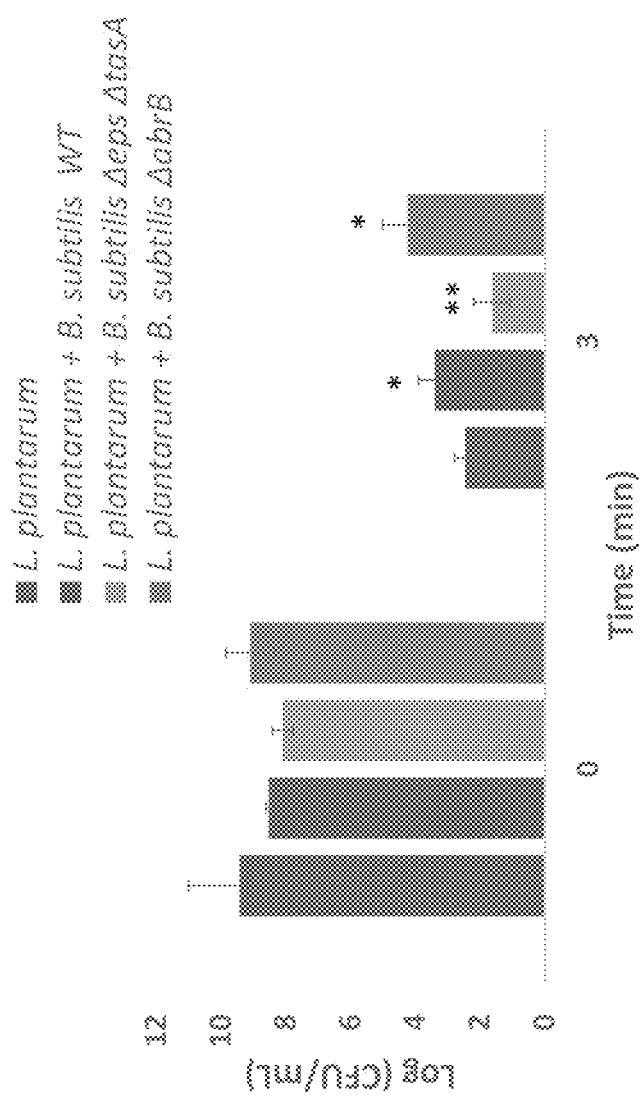
Figure 11B:
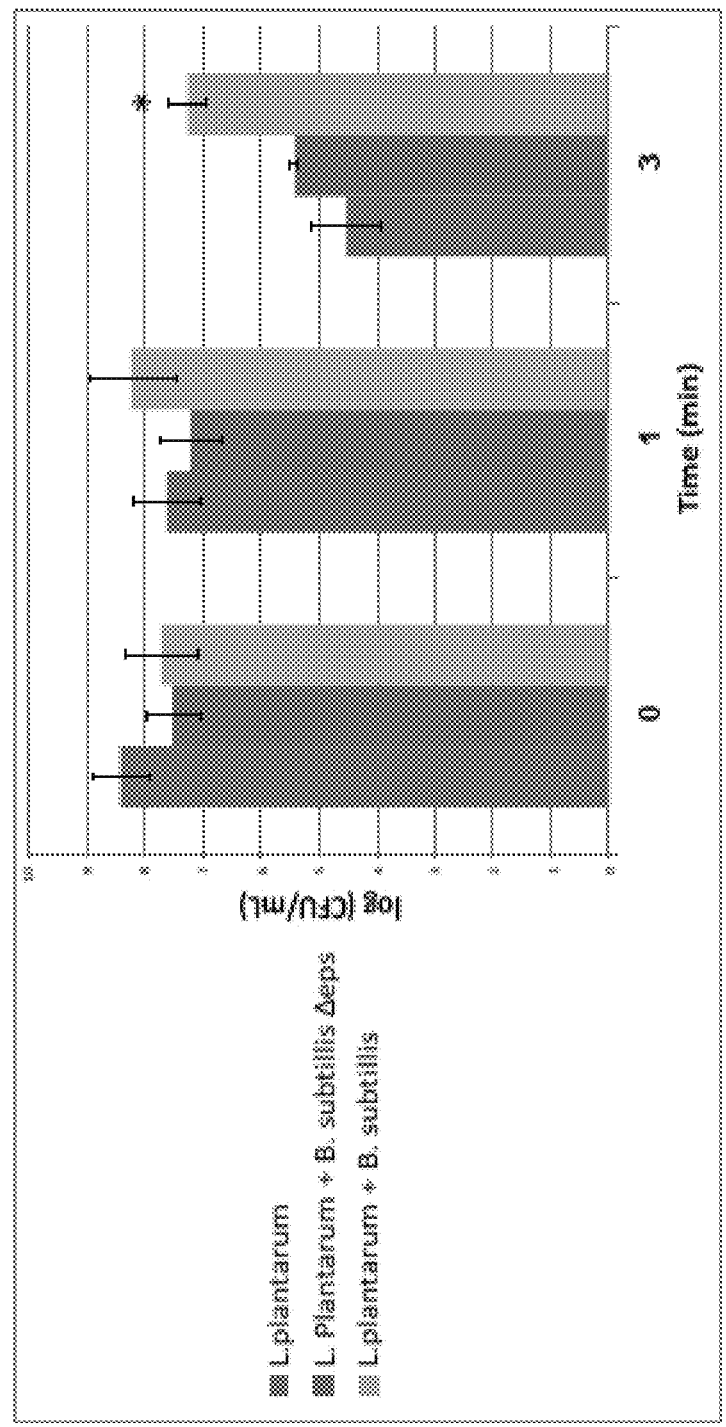
Figure 12:
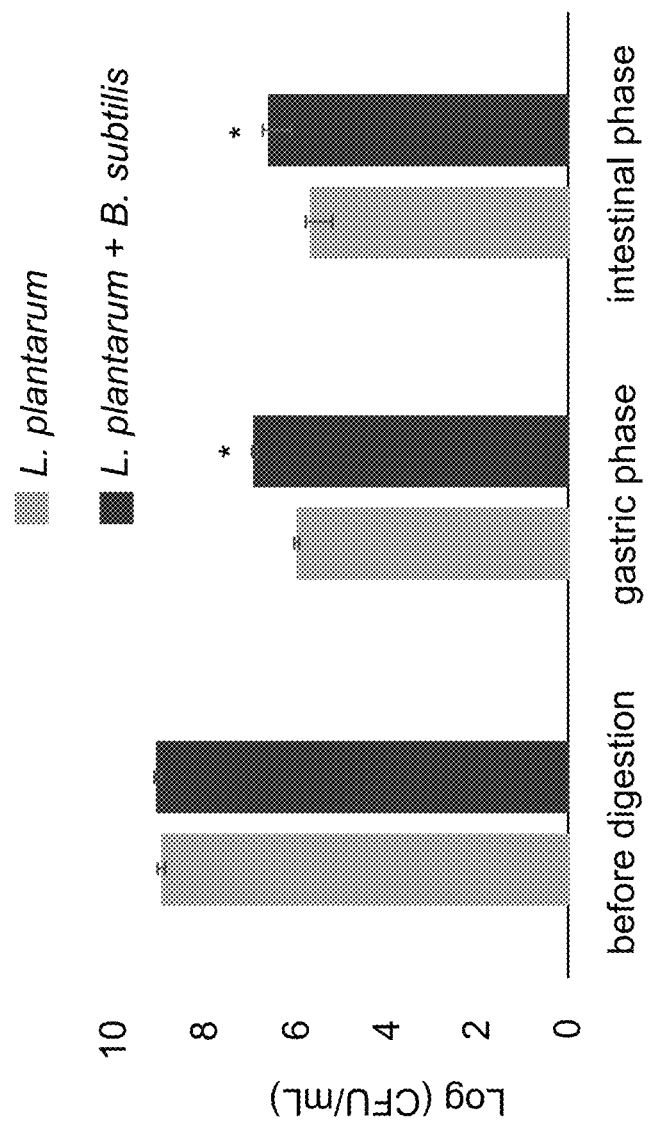
Figure 13:
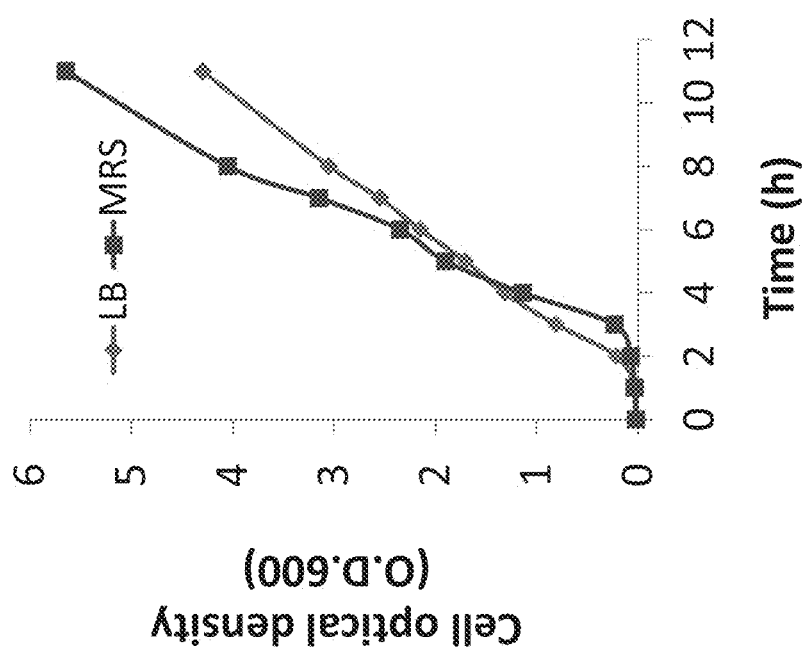

FIGS. 10A-B are graphs illustrating that dual species biofilm facilitates survival of *L. plantarum* exposed to unfavorable conditions. Survival of *L. plantarum* cells in presence or absence (control) of *B. subtilis* biofilm were determined during (A) heat treatment at 63° C. 1 to 3 min (B) storage at 4° C. for 21 days. The values presented are the average of at least three independent experiments performed in duplicates. *$p<0.05$ FIGS. 11A-B are graphs illustrating that the extracellular matrix of *B. subtilis* facilitates increased survival of *L. plantarum* during heat treatment. A. The effect of heat treatment at 63° C. for 3 min on WT *B. subtilis* and its derivatives, a mutant deficient in exopolysaccharide component and protein component of extracellular matrix ($\Delta eps\Delta tasA$) and a mutant deficient in a repressor of the matrix genes ($\Delta abrB$; overproduces biofilm matrix) was tested. The results presented are the average of at least three independent experiments performed in duplicates. *$p<0.05$. B. The samples were grown in milk for 18 h at 30° C., 20 rpm. Afterwards they were heat treated at 63° C. for 1 to 3 minutes. Control samples were not heat-treated. The number of viable *L. plantarum* cells was determined using CFU-method. *$p<0.05$ FIG. 12 is a graph illustrating that the presence of *B. subtilis* biofilm increases survival of *L. plantarum* during gastric and intestinal digestion in vitro (model system). Survival of *L. plantarum* cells in presence or absence (control) of *B. subtilis* biofilm were determined during gastro-intestinal digestion in vitro. The results presented are the average of three independent experiments performed in duplicates. *$p<0.05$ FIG. 13 is a graph of the growth curves of *B. subtilis* 3610NCIB in MRS (pH 7) and LB.

Figure 14:
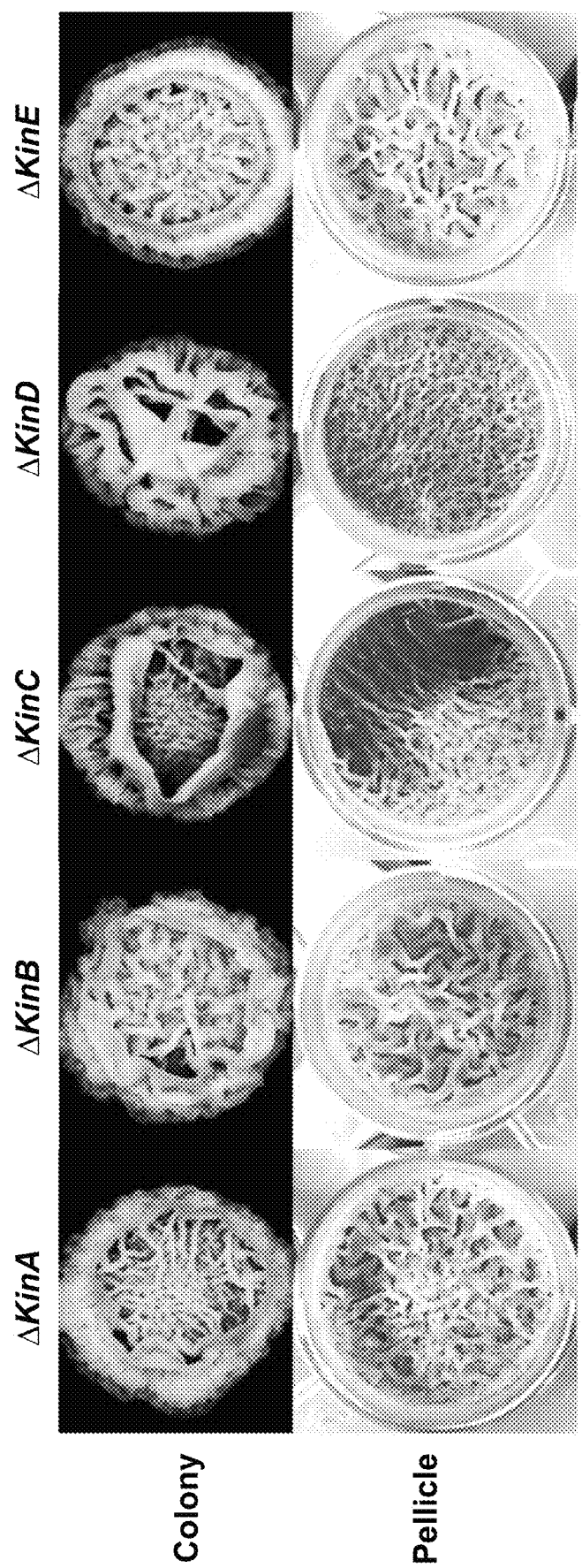

FIG. 14 are photographs illustrating the effect of mutations in Histidine kinases on colony surface architecture and pellicle formation in MRS pH 7.

FIGS. 15A-C and CLSM images of fluorescently tagged *B. subtilis* cells (Pspank-gfp) following 24 h incubation at LB medium in the presence and absence of acetoin.

FIGS. 16A-B are photographs illustrating that acetoin triggers the colony type biofilm formation by *Bacillus subtilis*

FIGS. 17A-D are photographs illustrating that the transcription of the tapA operon responsible for the matrix production in *B. subtilis* is highly upregulated by acetoin. CLSM images of *B. subtilis* cells that bear the PtapA-cfp transcriptional fusion, following 24 h incubation at LB medium that does not promote biofilm formation.

DESCRIPTION OF SPECIFIC EMBODIMENTS OF THE INVENTION

The present invention, in some embodiments thereof, relates to methods of generating bacterial compositions, more particularly, but not exclusively, to probiotic compositions, those beneficial to the environment and those used in industry.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Bacteria are economically important as these microorganisms are used by humans for many purposes. The beneficial uses of bacteria include the production of traditional foods such as yoghurt, cheese, and vinegar; biotechnology and genetic engineering, producing substances such as drugs and vitamins; agriculture; fibre retting; production of methane; bioremediation and biological control of pests.

To carry out their purpose, often times, bacteria are exposed to harsh conditions which reduce their viability and therefore their effectiveness.

For example, to assure a probiotic's beneficial effect in the body, these organisms must survive during food processing, storage and the passage through the upper gastrointestinal tract (GIT) and arrive alive to their site of action. However, previous studies have shown low survival level of probiotic bacteria in the final food product and a considerable loss in their viability to high acidic conditions of the stomach and high bile concentration in the small intestine. In addition, probiotics are usually available as dry bacterial powders prepared mainly by freeze drying which has been established as a procedure that may cause fatal injury to cells.

Whilst carrying out research on bacterial biofilms, the present inventors noticed that under appropriate conditions a biofilm-producing bacteria may incorporate a non-biofilm-producing bacteria into its biofilm rendering it more resistant to extreme temperatures (cold and heat; FIGS. 10A-B and 11A-B respectively).

Specifically, the present inventors co-cultured bacteria of the *B. subtilis* species together with the probiotic bacteria *L. plantarum*. They showed that under particular conditions the *B. subtilis* bacteria generated a biofilm in which the *L. plantarum* cells were incorporated within the extracellular matrix thereof (FIG. 9A). The biofilm-incorporated *L. plantarum* were shown to be both more heat-resistant and more cold-resistant, and further more acid-resistant than control, non-biofilm incorporated *L. plantarum*.

Taken together, the present inventors propose that biofilm-producing bacteria can be used to encapsulate a non-biofilm producing bacteria. Thus, the biofilm-producing bacteria serve as a protective carrier for the beneficial, non-biofilm producing bacteria.

Thus, according to a first aspect of the present invention, there is provided a method of preparing a bacterial composition comprising:

(a) in vitro co-culturing a beneficial bacteria with a biofilm-producing bacteria in a growth substrate under conditions that generate a biofilm which comprises the beneficial bacteria and the non-pathogenic bacteria;

(b) isolating the biofilm from the growth substrate, thereby preparing the bacterial composition.

The term "bacteria" as used herein refers to a prokaryotic microorganism, including archaea. The bacteria may be gram positive or gram negative. The bacteria may also be photosynthetic bacteria (e.g. cyanobacteria).

As used herein the term "beneficial bacteria" refers to any bacteria that bring about a positive effect on human beings.

In one embodiment, the beneficial bacteria do not produce a biofilm when propagated as a monoculture in a growth medium under standard culturing conditions.

In another embodiment, the beneficial bacteria do not produce a biofilm when propagated as a monoculture in a growth medium under culturing conditions that are optimal for their propagation.

In still another embodiment, the beneficial-bacteria utilize the KinD-Spo0A pathway (for example express the genes histidine kinase kinD, spo0F, spo0B and/or spo0A)—see for example Shemesh and Chai, 2013 Journal of Bacteriology, 2013, Vol 195, No.12 pages 2747-2754, the contents of which are incorporated herein by reference.

The beneficial bacteria may be one that is typically cultured in Man, Rogosa and Sharpe medium, MRS (solidified using agar or MRS broth).

The beneficial bacteria should typically not prevent (i.e. antagonize) the biofilm-forming capability of the biofilm-generating bacteria (e.g. *B. subtilis*). Methods of determining whether bacteria have antagonistic activity towards other bacteria when cultured together are known in the art (see for example FIGS. 1A-B). In one embodiment, the beneficial bacteria are not soil bacteria.

Any number of strains of beneficial bacteria may be cultured in the co-culture of this aspect of the present invention. In one embodiment, no more than 500 different strains of beneficial bacteria are cultured in a single culture, no more than 250 different strains of beneficial bacteria are cultured in a single culture, no more than 100 different strains of beneficial bacteria are cultured in a single culture, no more than 90 different strains of beneficial bacteria are cultured in a single culture, no more than 80 different strains of beneficial bacteria are cultured in a single culture, no more than 70 different strains of beneficial bacteria are cultured in a single culture, no more than 60 different strains of beneficial bacteria are cultured in a single culture, no more than 50 different strains of beneficial bacteria are cultured in a single culture, no more than 40 different strains of beneficial bacteria are cultured in a single culture, no more than 30 different strains of beneficial bacteria are cultured in a single culture, no more than 20 different strains of beneficial bacteria are cultured in a single culture, no more than 10 different strains of beneficial bacteria are cultured in a single culture, no more than 9 different strains of beneficial bacteria are cultured in a single culture, no more than 8 different strains of beneficial bacteria are cultured in a single culture, no more than 7 different strains of beneficial bacteria are cultured in a single culture, no more than 6 different strains of beneficial bacteria are cultured in a single culture, no more than 5 different strains of beneficial bacteria are cultured in a single culture, no more than 4 different strains of beneficial bacteria are cultured in a single culture, no more than 3 different strains of beneficial bacteria are cultured in a single culture, no more than 2 different strains of beneficial bacteria are cultured in a single culture only one strain of beneficial bacteria is cultured per single culture.

The beneficial bacterial strains of a single culture of this aspect of the present invention may belong to a single species or may belong to multiple species. Preferably, the beneficial bacterial strains of a culture belong to a single species of bacteria. In other embodiments multiple species of beneficial bacteria are cultured on a single culture. Preferably no more than 10 different species of beneficial bacteria are cultured in a single culture, no more than 9 different species of beneficial bacteria are cultured in a single culture, no more than 8 different species of beneficial bacteria are cultured in a single culture, no more than 7 different species of beneficial bacteria are cultured in a single culture, no more than 6 different species of beneficial bacteria are cultured in a single culture, no more than 5 different species of beneficial bacteria are cultured in a single culture, no more than 4 different species of beneficial bacteria are cultured in a single culture, no more than 3 different species of beneficial bacteria are cultured in a single culture, no more than 2 different species of beneficial bacteria are cultured in a single culture only one species of beneficial bacteria is cultured per single culture.

In one embodiment, the beneficial bacteria, when ingested promote the health of a human being. In another embodiment, the beneficial bacteria are used in industry to generate a product that is useful for human beings (e.g. methane, petroleum, insecticide etc.). In another embodiment, the beneficial bacteria are used in the food industry. In another embodiment, the beneficial bacteria are used in a silage inoculant. In still another embodiment, the beneficial bacteria are used in agriculture to support the growth of plants. In still another embodiment, the beneficial bacteria are used in bioremediation.

In one embodiment, the beneficial bacteria are probiotic bacteria.

The term "probiotic bacteria" as used herein refers to live bacteria which when administered in adequate amounts confer a health benefit on the host (e.g. human).

Among the principal mechanisms of probiotic action, it is possible to find the inhibition of enteric pathogens by the production of lactic acid, hydrogen peroxide and bacteriocins; competitive exclusion of enteric pathogens by blocking adhesion sites, competition for nutrients and modulation of the immune system, including inflammation reduction. They also provide benefits to the host, such as lactose intolerance alleviation; cholesterol decrease by assimilation, sustenance of the intestinal normal microbiota and dysbiosis ameliorating suppression of toxin production, degradation of toxin receptors in the intestine, preservation of normal intestinal pH, increase intestinal motility and help to maintain the integrity of the intestine permeability.

In one embodiment the beneficial bacteria belong to the order Lactobacillales (commonly known as lactic acid bacteria (LAB)). These bacteria are Gram-positive, low-GC, acid-tolerant, generally nonsporulating, non-respiring, either rod- or coccus-shaped bacteria that share common metabolic and physiological characteristics. These bacteria produce lactic acid as the major metabolic end product of carbohydrate fermentation.

Preferably the beneficial bacteria of the Lactobacillales order are ones which grow (and are typically cultured) in MRS agar (MRS).

Exemplary contemplated genera of the order Lactobacillales include, but are not limited to *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus*, and *Weissella*.

According to a preferred embodiment, the beneficial bacteria of this aspect of the present invention belong to the genus *Lactobacillus*. Exemplary species of *lactobacillus* contemplated by the present invention include but are not limited to *L. acetotolerans, L. acidifarinae, L. acidipiscis, L. acidophilus, L. agilis, L. algidus, L. alimentarius, L. amylolyticus, L. amylophilus, L. amylotrophicus, L. amylovorus, L. animalis, L. antri, L. apodemi, L. aviarius, L. bifermentans, L. brevis, L. buchneri, L. camelliae, L. casei, L. catenaformis, L. ceti, L. coleohominis, L. collinoides, L. composti, L. concavus, L. coryniformis, L. crispatus, L. crustorum, L. curvatus, L. delbrueckii* subsp. *bulgaricus, L. delbrueckii* subsp. *delbrueckii, L. delbrueckii* subsp. *lactis, L. dextrinicus, L. diolivorans, L. equi, L. equigenerosi, L. farraginis, L. farciminis, L. fermentum, L. fornicalis, L. fructivorans, L. frumenti, L. fuchuensis, L. gallinarum, L. gasseri, L. gastricus, L. ghanensis, L. hilgardii, L. homohiochii, L. iners, L. ingluviei, L. intestinalis, L. jensenii, L. johnsonii, L. kalixensis, L. kefiranofaciens, L. kefiri, L. kimchii, L. kitasatonis, L. kunkeei, L. leichmannii, L. lindneri, L. malefermentans, L. mali, L. manihotivorans, L. mindensis, L. mucosae, L. murinus, L. nagelii, L. namurensis, L. nantensis, L. oligofermentans, L. oris, L. panis, L. pantheris, L. parabrevis, L. parabuchneri, L. paracasei, L. paracollinoides, L. parafarraginis, L. parakefiri, L. paralimentarius, L. paraplantarum, L. pentosus, L. perolens, L. plantarum, L. pontis, L. protectus, L. psittaci, L. rennini L. reuteri, L. rhamnosus, L. rimae, L. rogosae, L. rossiae, L. ruminis, L. saerimneri, L. sakei, L. salivarius, L. sanfranciscensis, L. satsumensis, L. secaliphilus, L. sharpeae, L. siliginis, L. spicheri, L. suebicus, L. thailandensis, L. ultunensis, L. vaccinostercus, L. vaginalis, L. versmoldensis, L. vini, L. vitulinus, L. zeae* and *L. zymae*.

In one particular embodiment, the species of *Lactobacillus* is *L. plantarum*.

The beneficial bacteria of this aspect of the present invention may generate a fermentation product. Examples of fermentation products include but are not limited to prebiotics, biofuels, methanol, ethanol, propanol, butanol, alcohol fuels, proteins, recombinant proteins, vitamins, amino acids, organic acids (for e.g. lactic acid, propionic acid, acetic acid, succinic acid, malic acid, glutamic acid, aspartic acid and 3-hydroxypropionic acid), enzymes, antigens, antibiotics, organic chemicals, bioremediation treatments, preservatives and metabolites.

Thus, the beneficial bacteria may be genetically modified to express a beneficial polypeptide.

The beneficial polypeptides may be intracellular polypeptides (e.g., a cytosolic protein), transmembrane polypeptides, or secreted polypeptides. Heterologous production of proteins is widely employed in research and industrial settings, for example, for production of therapeutics, vaccines, diagnostics, biofuels, and many other applications of interest. Exemplary therapeutic proteins that can be produced by employing the subject compositions and methods, include but are not limited to certain native and recombinant human hormones (e.g., insulin, growth hormone, insulin-like growth factor 1, follicle-stimulating hormone, and chorionic gonadotropin), hematopoietic proteins (e.g., erythropoietin, C-CSF, GM-CSF, and IL-11), thrombotic and hematostatic proteins (e.g., tissue plasminogen activator and activated protein C), immunological proteins (e.g., interleukin), antibodies and other enzymes (e.g., deoxyribonuclease I). Exemplary vaccines that can be produced by the subject compositions and methods include but are not limited to vaccines against various influenza viruses (e.g., types A, B and C and the various serotypes for each type such as H5N2, H1N1, H3N2 for type A influenza viruses), HIV, hepatitis viruses (e.g., hepatitis A, B, C or D), Lyme disease, and human papillomavirus (HPV). Examples of heterologously produced protein diagnostics include but are not limited to secretin, thyroid stimulating hormone (TSH), HIV antigens, and hepatitis C antigens.

Proteins or peptides produced by the heterologous polypeptides can include, but are not limited to cytokines, chemokines, lymphokines, ligands, receptors, hormones, enzymes, antibodies and antibody fragments, and growth factors. Non-limiting examples of receptors include TNF type I receptor, IL-1 receptor type II, IL-1 receptor antagonist, IL-4 receptor and any chemically or genetically modified soluble receptors. Examples of enzymes include acetylcholinesterase, lactase, activated protein C, factor VII, collagenase (e.g., marketed by Advance Biofactures Corporation under the name Santyl); agalsidase-beta (e.g., marketed by Genzyme under the name Fabrazyme); dornase-alpha (e.g., marketed by Genentech under the name Pulmozyme); alteplase (e.g., marketed by Genentech under the name Activase); pegylated-asparaginase (e.g., marketed by Enzon under the name Oncaspar); asparaginase (e.g., marketed by Merck under the name Elspar); and imiglucerase (e.g., marketed by Genzyme under the name Ceredase). Examples of specific polypeptides or proteins include, but are not limited to granulocyte macrophage colony stimulating factor (GM-CSF), granulocyte colony stimulating factor (G-CSF), macrophage colony stimulating factor (M-CSF), colony stimulating factor (CSF), interferon beta (IFN-beta), interferon gamma (IFNgamma), interferon gamma inducing factor I (IGIF), transforming growth factor beta (IGF-beta), RANTES (regulated upon activation, normal T-cell expressed and presumably secreted), macrophage inflammatory proteins (e.g., MIP-1-alpha and MIP-1-beta), Leishmnania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF alpha type II receptor, erythropoietin (EPO), insulin and soluble glycoproteins e.g., gp120 and gp160 glycoproteins. The gp120 glycoprotein is a human immunodeficiency virus (WIV) envelope protein, and the gp160 glycoprotein is a known precursor to the gp120 glycoprotein. Other examples include secretin, nesiritide (human B-type natriuretic peptide (hBNP)) and GYP-I.

Contemplated bacteria for the expression of human interferon beta 1b include for example *E. coli*.

Contemplated bacteria for the expression of human interferon gamma include for example *E. coli*.

Contemplated bacteria for the expression of human growth hormone include for example *E. coli*.

Contemplated bacteria for the expression of human insulin include for example *E. coli*.

Contemplated bacteria for the expression of interleukin II include for example *E. coli*.

According to a particular embodiment, the beneficial polypeptide is an antibody (e.g. Humira, Remicade, Rituxan, Enbrel, Avastin, Herceptin).

Contemplated bacteria for the expression of antibodies include for example *E. coli, Bacillus brevis, Bacillus subtilis* and *Bacillus megaterium*.

Other beneficial bacteria contemplated by the present invention include those used as bacterial vaccines. Exemplary vaccines contemplated by the present invention include, but are not limited to Vivotif Berna Vaccine (typhoid vaccine, live), Prevnar 13 (pneumococcal 13-valent vaccine), Menactra (meningococcal conjugate vaccine), ActHIB (haemophilus b conjugate (prp-t) vaccine), Bexsero (meningococcal group B vaccine), Biothrax (anthrax vaccine adsorbed), Hiberix (haemophilus b conjugate (prp-t) vaccine), HibTITER (haemophilus b conjugate (hboc) vaccine), Liquid PedvaxHIB (haemophilus b conjugate (prp-omp) vaccine), MenHibrix (haemophilus b conjugate (prp-t) vaccine/meningococcal conjugate vaccine), Menomune A/C/Y/W-135 (meningococcal polysaccharide vaccine), Menveo (meningococcal conjugate vaccine), Pneumovax 23 (neumococcal 23-polyvalent vaccine), Prevnar (pneumococcal 7-valent vaccine), Te Anatoxal Berna (tetanus toxoid), Tetanus Toxoid Adsorbed (tetanus toxoid), TheraCys (bcg), Tice BCG (bcg), Trumenba (meningococcal group B vaccine), Typhim Vi (typhoid vaccine, inactivated), Vaxchora, cholera vaccine, live and Vivotif Berna (typhoid vaccine, live).

Other contemplated beneficial bacteria are those that are useful in bioremediation. Such remediation includes heavy metals, chemical, radiation and hydrocarbon contamination.

Examples of bacteria that may be used for bioremediation are listed herein below:

*Pseudomonas putida*: *Pseudomonas putida* is a gram-negative soil bacterium that is involved in the bioremediation of toluene, a component of paint thinner. It is also capable of degrading naphthalene, a product of petroleum refining, in contaminated soils.

*Dechloromonas aromatica*: *Dechloromonas aromatica* is a rod-shaped bacterium which can oxidize aromatics including benzoate, chlorobenzoate, and toluene, coupling the reaction with the reduction of oxygen, chlorate, or nitrate. It is the only organism able to oxidize benzene anaerobically. Due to the high propensity of benzene contamination, especially in ground and surface water, *D. aromatic* is especially useful for in situ bioremediation of this substance.

Nitrifiers and Denitrifiers: Industrial bioremediation is used to clean wastewater. Most treatment systems rely on microbial activity to remove unwanted mineral nitrogen compounds (i.e. ammonia, nitrite, nitrate). The removal of nitrogen is a two stage process that involves nitrification and denitrification. During nitrification, ammonium is oxidized to nitrite by organisms like *Nitrosomonas europaea*. Then, nitrite is further oxidized to nitrate by microbes like *Nitrobacter hamburgensis*. In anaerobic conditions, nitrate produced during ammonium oxidation is used as a terminal electron acceptor by microbes like *Paracoccus denitrificans*. The result is N2 gas. Through this process, ammonium and nitrate, two pollutants responsible for eutrophication in natural waters, are remediated.

*Deinococcus radiodurans*: *Deinococcus radiodurans* is a radiation-resistant extremophile bacterium that is genetically engineered for the bioremediation of solvents and heavy metals. An engineered strain of *Deinococcus radiodurans* has been shown to degrade ionic mercury and toluene in radioactive mixed waste environments.

In anaerobic conditions, nitrate produced during ammonium oxidation is used as a terminal electron acceptor by microbes like *Paracoccus denitrificans*. The result is dinitrogen gas. Through this process, ammonium and nitrate, two pollutants responsible for eutrophication in natural waters, are remediated.

*Methylibium petroleiphilum*: *Methylibium petroleiphilum* (formally known as PM1 strain) is a bacterium capable of methyl tert-butyl ether (MTBE) bioremediation. PM1 degrades MTBE by using the contaminant as the sole carbon and energy source.

*Alcanivorax borkumensis*: *Alcanivorax borkumensis* is a marine rod-shaped bacterium which consumes hydrocarbons, such as the ones found in fuel, and produces carbon dioxide. It grows rapidly in environments damaged by oil, and has been used to aid in cleaning the more than 830,000 gallons of oil from the Deepwater Horizon oil spill in the Gulf of Mexico. Other contemplated bacteria that can be used to clean up oil include *Colwellia* and *Neptuniibacter*.

As mentioned, the method of this aspect of the present invention contemplates culturing the beneficial bacteria with a biofilm-producing bacteria.

The term "biofilm" as used herein refers to a community of bacteria that are comprised (e.g. embedded or encapsulated) in a matrix of extracellular polymeric substances that they have produced. Typically, the bacteria when present in the biofilm exhibit an altered phenotype with respect to growth rate and gene transcription in comparison to freely floating planktonic bacteria. Examples of extracellular polymeric substances which may be present in the biofilm include exopolysaccharides (such as those synthesized by the products of the epsA-O operon) and amyloid fibers (such as those encoded by tapA-sipW-tasA operon). Thus, the matrix typically comprises extracellular DNA and protein, as well as carbohydrates.

It will be appreciated that the biofilm-producing bacteria may also be beneficial bacteria.

The biofilm-producing bacteria are typically of a different order and/or genus than the beneficial bacteria which are incorporated into the biofilm. Thus, the biofilm-producing bacteria and the beneficial bacteria may be of distinct strains, species, genus and/or order.

Preferably, the biofilm-producing bacteria is non-pathogenic (i.e. do not cause physical harm to, or disease in) a human being.

Any number of strains of biofilm-producing bacteria may be cultured in the co-culture of this aspect of the present invention. In one embodiment, no more than 500 different strains of biofilm-producing bacteria are cultured in a single culture, no more than 250 different strains of biofilm-producing bacteria are cultured in a single culture, no more than 100 different strains of biofilm-producing bacteria are cultured in a single culture, no more than 90 different strains of biofilm-producing bacteria are cultured in a single culture, no more than 80 different strains of biofilm-bacteria are cultured in a single culture, no more than 70 different strains of biofilm-producing bacteria are cultured in a single culture, no more than 60 different strains of biofilm-producing bacteria are cultured in a single culture, no more than 50 different strains of biofilm-producing bacteria are cultured in a single culture, no more than 40 different strains of biofilm-producing bacteria are cultured in a single culture, no more than 30 different strains of biofilm-producing bacteria are cultured in a single culture, no more than 20 different strains of biofilm-producing bacteria are cultured in a single culture, no more than 10 different strains of biofilm-producing bacteria are cultured in a single culture, no more than 9 different strains of biofilm-producing bacteria are cultured in a single culture, no more than 8 different strains of biofilm-producing bacteria are cultured in a single culture, no more than 7 different strains of the biofilm-producing bacteria are cultured in a single culture, no more than 6 different strains of the biofilm-producing bacteria are cultured in a single culture, no more than 5 different strains of the biofilm-producing bacteria are cultured in a single culture, no more than 4 different strains of the biofilm-producing bacteria are cultured in a single culture, no more than 3 different strains of biofilm-producing bacteria are cultured in a single culture, no more than 2 different strains of biofilm-producing bacteria are cultured in a single culture or only one strain of biofilm-producing bacteria are cultured per single culture.

The biofilm-producing bacterial strains of a single culture of this aspect of the present invention may belong to a single species or may belong to multiple species. Preferably, the biofilm-producing bacterial strains of a culture belong to a single species of bacteria. In other embodiments multiple species of biofilm-producing bacteria are cultured on a single culture. Preferably no more than 10 different species of biofilm-producing bacteria are cultured in a single culture, no more than 9 different species of biofilm-producing bacteria are cultured in a single culture, no more than 8 different species of biofilm-producing bacteria are cultured in a single culture, no more than 7 different species of biofilm-producing bacteria are cultured in a single culture, no more than 6 different species of biofilm-producing bacteria are cultured in a single culture, no more than 5 different species of biofilm-producing bacteria are cultured in a single culture, no more than 4 different species of biofilm-producing bacteria are cultured in a single culture, no more than 3 different species of biofilm-producing bacteria are cultured in a single culture, no more than 2 different species of biofilm-producing bacteria are cultured in a single culture or only one species of biofilm-producing bacteria is cultured per single culture.

In one embodiment, the biofilm-producing bacteria belong to the genus *Bacillus*.

As used herein, "the genus *Bacillus*" includes all members known to those of skill in the art, including but not limited to *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus*, *Amphibacillus*, *Aneurinibacillus*, *Anoxybacillus*, *Brevibacillus*, *Filobacillus*, *Gracilibacillus*, *Halobacillus*, *Paenibacillus*, *Salibacillus*, *Thermobacillus*, *Ureibacillus*, and *Virgibacillus*.

In one embodiment, the biofilm-producing bacteria are of the species *B. subtilis*.

Exemplary strains of *B. subtilis* contemplated by the present invention include, but are not limited to *B. paralicheniformis* MS303, *B. licheniformis* MS310, *B. paralicheniformis* S127, *B. subtilis* MS1577 and NCIB3610.

According to a particular embodiment, the biofilm-producing bacteria does not comprise the species *B. cereus*.

In order to generate a co-culture, typically both the beneficial culture and the biofilm-generating culture are cultured separately to generate a starter culture. The medium and conditions of the starter culture are typically selected so as to optimize growth of each of the bacteria.

Contemplated started cultures include a dried starter culture, a dehydrated starter culture, a frozen starter culture, or a concentrated starter culture.

The starter culture is grown for at least two hours, 4 hours, 8 hours, 12 hours until a sufficient amount of bacteria are propagated.

According to a particular embodiment, the method includes a method of co-culturing, whereby the beneficial bacteria is of the genus *lactobacillus* (e.g. the species *L. plantarum*) and the biofilm-producing bacteria is of the genus *Bacillus* (e.g. of the species *B. subtilis*).

The method of co-culturing the beneficial bacteria with the biofilm producing bacteria is selected such that it enables the proliferation of both types of microorganisms and incorporation of both microorganisms into the biofilm.

In one embodiment, the co-culturing is carried out in (or on) a growth substrate that is typically used to culture the beneficial bacteria. The growth substrate may be a solid or a liquid medium.

Examples of growth substrates that can be used to culture bacteria include but are not limited to MRS medium, LB medium, TBS medium, yeast extract, soy peptone, casein peptone and meat peptone.

Further examples of media are listed in Table 1 herein below.

TABLE 1

*Abiotrophia* media-Recipe for medium appropriate for growth of *Abiotrophia* genus
Acetamide Medium-Recipe for Acetamide medium.
*Acetobacter* Medium-Recipe for medium appropriate for the growth of *Acetobacter* genus.
*Actinoplanes* Medium-Media used to grow certain *Actinoplanes* species
*Agrobacterium* Agar Recipe-Agar appropriate for growth of *Agrobacterium* genus
*Alicyclobacillus* Agar-Recipe for *Alicyclobacillus* Agar.
*Alicyclobacillus* Medium-Recipe for *Alicyclobacillus* Medium.
Allantoin mineral agar-Recipe for the preparation of Allantoin minimal agar.
Allantoin mineral medium-Recipe for the preparation of allantoin minimal medium.
Ashbya Full Medium-Recipe for the production of Ashbya full medium.
*Azotobacter* Agar-Agar appropriate for growth of *Azobacter* genus.
Bennett's Medium-media used for growth of some *Actinoplanes* species.
*Bacillus* agar-Agar used to grow some *Bacillus* species.
*Bacillus* broth-Agar used to grow some *Bacillus* species.
*Bacillus schlegelii* Medium-Medium appropriate for the growth of *Bacillus schlegelii*.
*Bifidobacterium* Medium-Recipe for *Bifidobacterium* medium.
Blue green algae agar-Recipe for blue green algae agar.
Blue green algae broth-Recipe for blue green algae broth.
Brain Heart Infusion Glucose Agar-Recipe for Brain Heart Infusion Glucose Agar.
*Caulobacter* Agar-Recipe for *Caulobacter* Agar.
*Caulobacter* Medium-Recipe for *Caulobacter* Medium.
Cantharellus Agar Recipe-Recipe for Cantharellus agar.
CASO agar-Recipe for CASO agar.
*Clostridium thermocellum* Medium-Recipe for medium appropriate for growth of *Clostridium thermocellum*
*Corynebacterium* agar-Recipe for *Corynebacterium* agar.
Creatinine Medium-Recipe for the production of creatinine medium.
Czapek Agar (CZA)-Recipe for Czapek Agar (CZA).
*Desulfovibrio* Medium-Recipe for *Desulfovibrio* Medium.
*Gluconobacter* agar-Recipe for *Gluconobacter* agar.
Glucose Peptone Yeast Extract Agar (GPYA)-Recipe for Glucose Peptone Yeast Extract Agar (GPYA).
Glucose Yeast Extract Agar-Recipe for Glucose Yeast Extract Agar.
*Halobacterium* agar-Recipe for the preparation of *Halobacterium* agar.
*Halobacteria* Medium-Recipe for *Halobacteria* Medium.
LB Agar-Recipe for the preparation of LB agar bacterial media.
LB broth-Recipe for the preparation of LB broth bacterial media.
LB broth (low salt)-Recipe for the preparation of low salt LB broth bacterial media.
Luminous Medium-Recipe for Luminous Medium.
M17 media-Recipe for the preparation of M17 media.
M9 minimal media-Minimal salts bacterial media.
Mannitol agar-Recipe for mannitol agar.
Mannitol broth-Recipe for mannitol broth.

TABLE 1-continued

Marine agar-Recipe for marine agar. Used for the growth of several marine bacteria.
Marine broth-Recipe for marine broth. Used for the growth of several marine bacteria.
Methylamine Salts Agar-Recipe for methylamine salts agar
Methylamine Salts Medium-Recipe for methylamine salts medium
Modified Chopped Meat Medium-Used for the growth of several anaerobic bacteria.
MY medium-Maltose yeast extract bacterial growth medium.
N4 Mineral Medium-Recipe for the produciton of N4 mineral medium.
*Nitrosomonas europaea* medium-Recipe for the production of *Nitrosomonas europaea* medium.
Nutrient agar-Recipe for nutrient agar suitable for growth of many bacterial species.
Nutrient broth-Recipe for nutrient broth suitable for growth of many bacterial species.
MRS media-Recipe for MRS media. MRS media has been used for the recovery of lactic acid bacteria (LAB) from various food products.
MS-Medium-Recipe for MS-medium.
N-Z amine agar with soluble starch and glucose-Agar used to grow some *Actinomadura* species
NZCYM-NZ amine, NaCl, bacto-yeast extract, casamino acids, and magnesium sulfate.
NZM-NZ amine, NaCl, and magnesium sulfate.
NZYM-NZ amine, NaCl, bacto-yeast extract, and magnesium sulfate.
Oatmeal agar-agar used to grow some *Actinomadura* species.
*Oenococcus* Medium-Recipe for the preparation of *Oenococcus* medium.
Osmophilic Agar-Recipe for Osmophilic Agar.
Osmophilic Medium-Recipe for Osmophilic Medium.
Phenol red lactose broth-turns yellow when lactose is fermented.
Potato-Carrot Medium-agar used to grow some *Actinoplanes* species.
*Propionibacterium* Agar Recipe-Agar appropriate for the growth of *Propionibacterium*.
*Propionibacterium* Medium Recipe-Medium appropriate for the growth of *Propionibacterium*.
PYS agar-agar used to grow some *Actinomadura* species.
R Medium-R Medium Recipe.
Rolled Oats Mineral Agar-Recipe for Rolled Oats Mineral Agar.
Saccharose agar-Recipe for the production of saccharose agar
Saccharose medium-Recipe for the production of saccharose medium
SOB media-Tryptone/yeast extract bacterial media.
SOC media-Tryptone/yeast extract bacterial media.
5% Sorbitol agar-Recipe for the production of 5% sorbitol agar.
5% Sorbitol medium-Recipe for the production of 5% sorbitol medium.
Sour Dough Medium-Recipe for the preparation of sour dough medium.
Starch-Mineral Salt (STMS) Agar-Recipe for starch-mineral salt (STMS) agar.
Styrene Mineral Salts Medium-Recipe for Styrene Mineral Salts medium.
Terrific broth-Recipe for the preparation of terrific broth bacterial media.
*Thermus* Agar-Recipe for agar appropriate for the growth of *Therums* genus
*Thermus* Medium-Recipe for media appropriate for the growth of *Therums* genus
*Thiobacillus* Medium F2-Recipe for the production of *Thiobacillus* medium F2
Tomato Juice Agar-Recipe for the preparation of tomato juice agar.
Tomato Juice Medium-Recipe for the preparation of tomato juice medium.
Tomato Juice Yeast Extract Agar-Recipe for the preparation of tomato juice yeast extract agar.
Tomato Juice Yeast Extract Medium-Recipe for the preparation of tomato juice yeast extract medium.
TSY agar-Trypticase soy yeast agar Recipe.
TSY broth-Trypticase soy yeast broth Recipe.
TYG Medium-Tryptone, yeast, glucose bacterial growth medium.
TYX Medium-Tryptone, yeast, xylose bacterial growth medium.
Urea Medium-Recipe for the preparation of urea medium
Uric Acid Medium-Recipe for the preparation of uric acid medium
Whey Agar-Recipe for the preparation of whey agar.
Whey Medium-Recipe for the preparation of whey medium.
Wickerham Salt Agar-Recipe for Wickerham Salt Agar.
Wickerham Salt Medium-Recipe for Wickerham Salt Medium.
Yeast Extract Glucose Medium-Yeast Extract Glucose medium recipe
YEL Agar-Recipe for YEL Agar.
YMF agar recipe-Recipe for preparation of YMF agar.
YMF medium recipe-Recipe for preparation of YMF medium.
YMG agar-Recipe for yeast and malt extract with glucose agar. This agar is used for a number of *Streptomyces* species.
YMG media-Recipe for yeast and malt extract with glucose media. This media is used for a number of *Streptomyces* species.
YPD Agar-Yeast extract/peptone/dextrose bacterial agar.
YPD media-Yeast extract/peptone/dextrose bacterial media.
YPG media-Yeast extract/peptone/galactose bacterial media.
YPM Agar-Recipe for YPM agar.
YPM Medium-Recipe for YPM medium.
YT (2x)-Yeast extract/tryptone bacterial media.

Thus, for example in the case of the beneficial bacteria being of the genus *lactobacillus* (e.g. the species *L. plantarum*) and the biofilm-producing bacteria being of the genus *Bacillus* (e.g. of the species *B. subtilis*), the co-culture may be carried out in a growth substrate which comprises LBGM, milk or MRS. Other media that can be used to generate the co-culture of the present invention include MSgg minimal medium (Shemesh, M., et al (2010). *J Bacteriol* 192, 6352-6356); LB enriched with lactose: Duanis-Assaf D., et al (2016) Front. Microbiol. 6: 1517; LB with addition of butyric acid: Pasvolsky R., et al., Int. J. Food Microbiol. 181C: 19-27. Typically, the culturing conditions are selected that encourage incorporation of both the different bacteria into the biofilm.

Thus according to another aspect of the present invention there is provided a method of selecting an agent or culturing condition which is advantageous for preparing a bacterial composition, the method comprising co-culturing beneficial bacteria with a biofilm-producing bacteria in a growth substrate in the presence of the agent or under the culturing condition so as to generate a biofilm comprising the beneficial bacteria and the biofilm-producing bacteria, wherein a change in a property of the biofilm is indicative of the agent or culturing condition being advantageous for preparing the bacterial composition.

Exemplary conditions of the co-culture that may be altered include the properties of the surface on which the culture is carried out (for example the surface chemistry of the solid surface, including but not limited to functional groups, electrostatic charge, coating; surface roughness, surface topography, including but not limited to grooves, cavities, ridges, pores, hexagonally packed (HP) pillars, equilateral triangles surrounded by HP pillars, and the Sharklet topography etc.). The solid surface may be of a defined geometry and/or topography such that it promotes encapsulation/incorporation of the beneficial bacteria into the biofilm. Furthermore, the solid surface may be of a defined geometry and/or topography such that it promotes generation of a biofilm of a particular thickness. Other topographical patterns contemplated by the present invention are described in Graham and Cady, Coatings, 2014, 4, pages 37-59, the contents of which are incorporated herein by reference.

Exemplary solid surfaces on which the culturing can be carried out include a wide range of substrates, ranging from various polymeric materials (silicone, polystyrene, polyurethane, and epoxy resins) to metals and metal oxides (silicon, titanium, aluminum, silica, and gold). Fabrication techniques (soft lithography and double casting molding techniques, microcontact printing, electron beam lithography, nanoimprint lithography, photolithography, electrodeposition methods, etc.) can be carried out on such materials in order to alter the topography of the solid surface.

Other conditions of the co-culture that may be altered include, but are not limited to environmental parameters such as pH, nutrient concentration, the ratio between the beneficial bacteria:biofilm producing bacteria and temperature.

In one embodiment, the co-culturing is carried out in a bioreactor.

As used herein, the term "bioreactor" refers to an apparatus adapted to support the biofilm of the invention.

The bioreactor will generally comprise one or more supports for the biofilm which may form a film thereover, and wherein the support is adapted to provide a significant surface area to enhance the formation of the biofilm. The bioreactors of the invention may be adapted for continuous throughput.

It will be appreciated that when the biofilm is generated in a bioreactor system, the conditions of the co-culture can be altered by altering the microfluidics (e.g. sheer stress) of the system.

As mentioned, the agents or conditions are selected that bring about an advantageous change in a property of the biofilm. In one embodiment, the property is an amount of biofilm. In one embodiment, the property is a thickness of biofilm. In another embodiment, the property is a density of the biofilm. In yet another embodiment, the property is the rate in which the biofilm is formed. In still another embodiment, the property is the amount of beneficial bacteria which is incorporated into the biofilm. In still another embodiment, the property is the resistance to temperature and/or pH.

In still another embodiment, the property is the amount of beneficial bacteria released from the biofilm over a period of time. This may be of particular relevance when a controlled release of the beneficial bacteria is required. For example, it may be advantageous to incorporate bacteria which are beneficial for the skin, scalp or dental applications in biofilms of which the rate of release of the beneficial bacteria therefrom is selected for maximum therapeutic effect.

The present inventors have now found that altering the pH of the growth substrate to higher than 6, encourages bacteria that utilize the KinD-Spo0A pathway (e.g. being of the genus *Bacillus*, such as of the species *B. subtilis*) to be incorporated into a biofilm when cultured in MRS.

In one embodiment, the co-culturing of the beneficial bacteria being of the genus *lactobacillus* (e.g. the species *L. plantarum*) and the biofilm-producing bacteria being of the genus *Bacillus* (e.g. of the species *B. subtilis*), carried out in, or on LBGM, milk or MRS (and more specifically MRS) is effected at a pH of between 6.5 and 9; 6.5 and 8; 6.5 and 7.5; 6.8 and 9; 6.8 and 8; 6.8 and 7.5.

The co-culturing of this aspect of the present invention may be carried out in the presence of additional agents that serve to increase propagation of the bacteria and/or enhance biofilm formation. Such agents include for example acetoin.

The amount of acetoin and the timing of addition may be altered so as to promote optimal biofilm production. In one embodiment, about 0.01-5% acetoin is used. In another embodiment, about 0.01-4% acetoin is used. In another embodiment, about 0.01-3% acetoin is used. In another embodiment, about 0.01-2% acetoin is used. In another embodiment, about 0.01-1% acetoin is used. In another embodiment, about 0.01-0.5% acetoin is used.

Thus, the present inventors contemplate a culture comprising acetoin, a biofilm comprising a *Bacillus* bacteria and a culture medium. In one embodiment, the culture medium is one which is mentioned in Table 1 (for example LB).

In one embodiment, about 0.05-5% acetoin is used. In another embodiment, about 0.05-4% acetoin is used. In another embodiment, about 0.05-3% acetoin is used. In another embodiment, about 0.05-2% acetoin is used. In another embodiment, about 0.05-1% acetoin is used. In another embodiment, about 0.05-0.5% acetoin is used.

In one embodiment, about 0.1-5% acetoin is used. In another embodiment, about 0.1-4% acetoin is used. In another embodiment, about 0.1-3% acetoin is used. In another embodiment, about 0.1-2% acetoin is used. In another embodiment, about 0.1-1% acetoin is used. In another embodiment, about 0.1-0.5% acetoin is used.

The co-cultures of this aspect of the present invention are propagated for a length of time sufficient to generate a biofilm which incorporates both the beneficial bacteria and the biofilm generating bacteria.

According to one embodiment the co-cultures are grown to maximal plateau growth phase of the beneficial bacteria, at which time they may be harvested for maximal biofilm production.

According to another embodiment the co-cultures are grown to maximal plateau growth phase of the biofilm-producing bacteria, at which time they may be harvested for maximal biofilm production.

Thus, the bacteria may be cultured for at least 3 hours, at least 6 hours, at least 12 hours, at least 24 hours, 2 days, 3 days, 4 days, 5 days, 6 days or 7 days or longer. In one embodiment, the bacteria are not cultured for longer than 1 week, 2 weeks, 3 weeks, 4 weeks, 5 weeks or 6 weeks.

Once sufficient quantities of beneficial bacteria are propagated (and encapsulated in the biofilm), the biofilm is harvested (i.e. removed from the growth substrate).

Following isolation from the growth substrate, the biofilm (and/or bacteria incorporated therein) may be subject to drying (i.e. dehydrating), freezing, spray drying, or freeze-drying. Preferably, the biofilm is treated in a way that preserves the viability of the bacteria.

Thus, according to another aspect of the present invention there is provided a bacterial composition obtainable according to the methods described herein.

The biofilm-producing bacteria is present in the bacterial composition in an amount of from $10^3$ to $10^{15}$ colony forming units per gram of the bacterial composition (e.g. probiotic composition).

The amount (in weight) of non-cellular material (e.g. exopolysaccharides and/or amyloid fibers) in the composition may be higher than the amount (in weight) of cellular material (e.g. bacterial cells). For example, the weight of non-cellular material (e.g. exopolysaccharides and/or amyloid fibers) in the composition may be at least 5%, 10%, 20%, 30%, 40%, 50%, 60%, 70%, 80%, 90% or 100% higher than the weight of cellular material (e.g. bacterial cells) in the composition.

The amount (in weight) of non-cellular material (e.g. exopolysaccharides and/or amyloid fibers) in the composition may be lower than the amount (in weight) of cellular material (e.g. bacterial cells). For example, the weight of cellular material (e.g. bacterial cells) in the composition may be at least 5%, 10%, 20%, 30%, 40%, 50%, 60%, 70%, 80%, 90% or 100% higher than the weight of non-cellular material (e.g. e. exopolysaccharides and/or amyloid fiber) in the composition.

Thus, the weight ratio of non-cellular material (e.g. exopolysaccharides):bacterial cells in the compositions described herein may be between 99:1-1:99. In some embodiments the weight ratio of non-cellular material (e.g. exopolysaccharides): bacterial cells in the compositions described herein may be between 99:1-50:50. In some embodiments the weight ratio of non-cellular material (e.g. exopolysaccharides):bacterial cells in the compositions described herein may be between 99:1-70:30.

In one embodiment, the bacterial composition is a probiotic composition.

In some embodiments, the probiotic composition comprises from about $10^3$ to $10^{15}$ colony forming units ("CFUs") of the biofilm-producing microorganism per gram of finished product. In some embodiments, the probiotic composition comprises from about $10^4$ to about $10^{14}$ CFUs of the biofilm-producing microorganism per gram of finished product. In some embodiments, the probiotic composition comprise from about $10^5$ to about $10^{15}$ CFUs of biofilm-producing microorganism per gram of finished product. In some embodiments, the probiotic composition comprises from about $10^6$ to $10^{11}$ colony forming units of the biofilm-producing microorganism per gram of finished product. In some embodiments, the probiotic composition comprises from about $10^2$ to about $10^5$ colony forming units of the biofilm-producing microorganism per gram of finished product.

It will be appreciated that at least 20%, 30%, 40%, 50%, 60%, 70%, 80%, 90% or more of the beneficial bacteria of the composition are viable (i.e. propagate). Furthermore, at least 20%, 30%, 40%, 50%, 60%, 70%, 80%, 90% or more of the biofilm-producing bacteria of the composition are viable (i.e. propagate).

According to a particular embodiment, the bacterial composition is a probiotic composition.

Exemplary beneficial bacteria that may be present in the probiotic composition are those that belong to the genus *lactobacillus* (as described herein above).

The probiotic composition may comprise additional beneficial bacteria such as those belonging to the *Bifidobacterium* genus. Contemplated species of *Bifidobacterium* that may be present in the probiotic composition of this aspect of the present invention include, but are not limited to *Bifidobacterium longum, Bifidobacterium bifidum, Bifidobacterium breve, Bifidobacterium infantis, Bifidobacterium adolecentis, Bifidobacterium lactis*, and *Bifidobacterium animalis*. In some embodiments, the probiotic composition comprises a species that belongs to the genus *lactobacillus* e.g. *Lactobacillus plantarum* and at least two microorganisms selected from the following *Bifidobacterium longum, Bifidobacterium bifidum, Bifidobacterium breve, Bifidobacterium infantis, Bifidobacterium adolecentis, Bifidobacterium lactis*, and *Bifidobacterium animalis*.

In one embodiment, the bacterial compositions disclosed herein are in any form suitable for administering the composition to a mammalian subject. In some embodiments, the composition is in the form of a tablet, a powder or a liquid. If provided as a powder, combining the powder with a suitable liquid (e.g., liquid dairy product, fruit or vegetable juice, blended fruit or vegetable juice product, etc.) is specifically contemplated.

In some embodiments, the bacterial compositions disclosed herein are administered to a subject prior to, concomitant with or following administration of an antibiotic agent. The conditions of the co-culture may be such that the biofilm which is generated releases the beneficial bacteria in the body such that they are not subject to the activity of the antibiotic agent.

In some embodiment, the bacterial compositions described herein are formulated for topical administration—e.g. in a cream, a gel, a lotion, a shampoo, a rinse. The bacterial compositions may be administered to the skin or the scalp. The bacterial compositions may be useful for dental applications. For such applications they may be administered to the gums.

In some embodiments the compositions described herein are incorporated into a food product. The term "food product" as used herein refers to any substance containing nutrients that can be ingested by an organism to produce energy, promote health and wellness, stimulate growth, and maintain life. The term "enriched food product" as used herein refers to a food product that has been modified to include the composition comprising composition described herein, which provides a benefit such as a health/wellness-promoting and/or disease-preventing/mitigating/treating property beyond the basic function of supplying nutrients.

The probiotic composition can be incorporated into any food product. Exemplary food products include, but are not limited to, protein powder (meal shakes), baked goods (cakes, cookies, crackers, breads, scones and muffins), dairy-type products (including but not limited to cheese, yogurt, custards, rice pudding, mousses, ice cream, frozen yogurt, frozen custard), desserts (including, but not limited to, sherbet, sorbet, water-ices, granitas and frozen fruit purees), spreads/margarines, pasta products and other cereal products, meal replacement products, nutrition bars, trail mix, granola, beverages (including, but not limited to, smoothies, water or dairy beverages and soy-based beverages), and breakfast type cereal products such as oatmeal. For beverages, the probiotic composition described herein may be in solution, suspended, emulsified or present as a solid.

In one embodiment, the enriched food product is a meal replacement product. The term "meal replacement product" as used herein refers to an enriched food product that is intended to be eaten in place of a normal meal. Nutrition bars and beverages that are intended to constitute a meal replacement are types of meal replacement products. The term also includes products which are eaten as part of a meal replacement weight loss or weight control plan, for example snack products which are not intended to replace a whole meal by themselves, but which may be used with other such products to replace a meal or which are otherwise intended to be used in the plan. These latter products typically have a calorie content in the range of from 50-500 kilocalories per serving.

In another embodiment, the food product is a dietary supplement. The term "dietary supplement" as used herein refers to a substance taken by mouth that contains a "dietary ingredient" intended to supplement the diet. The term "dietary ingredients" includes, but is not limited to, the composition comprising the probiotic composition as described herein as well as vitamins, minerals, herbs or other botanicals, amino acids, and substances such as enzymes, organ tissues, glandulars, and metabolites.

In yet another embodiment, the food product is a medical food. The term "medical food" as used herein means a food which is formulated to be consumed or administered entirely under the supervision of a physician and which is intended for the specific dietary management of a disease or condition for which distinctive nutritional requirements, based on recognized scientific principles, are established by medical evaluation.

It is also well established that the addition of probiotic microorganisms to animal feed can improve animal efficiency and health. Specific examples include increased weight gain-to-feed intake ratio (feed efficiency), improved average daily weight gain, improved milk yield, and improved milk composition by dairy cows as described by U.S. Pat. Nos. 5,529,793 and 5,534,271. The administration of probiotic organisms can also reduce the incidence of pathogenic organisms in cattle, as reported by U.S. Pat. No. 7,063,836.

Thus, according to another embodiment, the probiotic composition described herein can be incorporated into an animal feed.

In one embodiment, the probiotic composition is designed for continual or periodic administration to ruminal, cecal or intestinal fermentors throughout the feeding period in order to reduce the incidence and severity of diarrhea and/or overall health. In this embodiment, the probioitic composition can be introduced into the rumen, cecum and/or intestines of the animal.

In yet another embodiment, the probiotic composition described herein are incorporated into a pharmaceutical product or composition. Pharmaceutical compositions comprise a prophylactically or therapeutically effective amount of the composition described herein and typically one or more pharmaceutically acceptable carriers or excipients (which are discussed below).

The disclosure contemplates formulations of the bacterial compositions described herein that are, in some embodiments, powdered, tableted, encapsulated or otherwise formulated for oral administration. The compositions may be provided as pharmaceutical compositions, nutraceutical compositions (e.g., a dietary supplement), or as a food or beverage additive, as defined by the U.S. Food and Drug Administration. The dosage form for the above compositions are not particularly restricted. For example, liquid solutions, suspensions, emulsions, tablets, pills, capsules, sustained release formulations, powders, suppositories, liposomes, microparticles, microcapsules, sterile isotonic aqueous buffer solutions, and the like are all contemplated as suitable dosage forms.

The compositions typically include one or more suitable diluents, fillers, salts, disintegrants, binders, lubricants, glidants, wetting agents, controlled release matrices, colorings, flavoring, carriers, excipients, buffers, stabilizers, solubilizers, commercial adjuvants, and/or other additives known in the art.

Any pharmaceutically acceptable (i.e., sterile and acceptably non-toxic as known in the art) liquid, semisolid, or solid diluent that serves as a pharmaceutical vehicle, excipient, or medium can be used. Exemplary diluents include, but are not limited to, polyoxyethylene sorbitan monolaurate, magnesium stearate, calcium phosphate, mineral oil, cocoa butter, and oil of theobroma, methyl- and propylhydroxybenzoate, talc, alginates, carbohydrates, especially mannitol, .alpha.-lactose, anhydrous lactose, cellulose, sucrose, dextrose, sorbitol, modified dextrans, gum acacia, and starch.

Pharmaceutically acceptable fillers can include, for example, lactose, microcrystalline cellulose, dicalcium phosphate, tricalcium phosphate, calcium sulfate, dextrose, mannitol, and/or sucrose. Salts, including calcium triphosphate, magnesium carbonate, and sodium chloride, may also be used as fillers in the pharmaceutical compositions.

Binders may be used to hold the composition together to form a hard tablet. Exemplary binders include materials from organic products such as acacia, tragacanth, starch and gelatin. Other suitable binders include methyl cellulose (MC), ethyl cellulose (EC) and carboxymethyl cellulose (CMC).

In some embodiments, an enriched food product further comprises a bioavailability enhancer, which acts to increase the absorption of the sorbable natural product(s) by the body. Bioavailability enhancers can be natural or synthetic compounds. In one embodiment, the enriched food product comprising the composition described herein further comprises one or more bioavailability enhancers in order to enhance the bioavailability of the bioactive natural product(s).

Natural bioavailability enhancers include ginger, caraway extracts, pepper extracts and chitosan. The active compounds in ginger include 6-gingerol and 6-shogoal. Caraway oil can also be used as a bioavailability enhancer (U.S. Patent Application 2003/022838). Piperine is a compound derived from pepper (Piper nigrum or Piper longum) that acts as a bioavailability enhancer (see U.S. Pat. No. 5,744,161). Piperine is available commercially under the brand name Bioperine™ (Sabinsa Corp., Piscataway, N.J.). In some embodiments, the natural bioavailability enhancers is present in an amount of from about 0.02% to about 0.6% by weight based on the total weight of enriched food product.

Examples of suitable synthetic bioavailability enhancers include, but are not limited to surfactants including those composed of PEG-esters such as are commercially available under the tradenames: Gelucire™, Labrafil™, Labrasol™, Lauroglycol™, Pleurol Oleique™ (Gattefosse Corp., Paramus, N.J.) and Capmul™ (Abitec Corp., Columbus, Ohio).

The amount and administration regimen of the composition is based on various factors relevant to the purpose of administration, for example human or animal age, sex, body weight, hormone levels, or other nutritional need of the human or animal. In some embodiments, the composition is administered to a mammalian subject in an amount from about 0.001 mg/kg body weight to about 1 g/kg body weight.

A typical regimen may comprise multiple doses of the composition. In one embodiment, the composition is administered once per day. The composition may be administered to an individual at any time. In some embodiments, the composition is administered concurrently, or prior to or at the consumption of a meal.

In some embodiments the bacterial compositions of this aspect of the present invention are formulated for use as an agricultural product. The bacterial compositions may be added to an agricultural carrier such as soil or plant growth medium. Other agricultural carriers that may be used include fertilizers, plant-based oils, humectants, or combinations thereof. Alternatively, the agricultural carrier may be a solid, such as diatomaceous earth, loam, silica, alginate, clay, bentonite, vermiculite, seed cases, other plant and animal products, or combinations, including granules, pellets, or suspensions. Mixtures of any of the aforementioned ingredients are also contemplated as carriers, such as but not limited to, pesta (flour and kaolin clay), agar or flour-based pellets in loam, sand, or clay, etc. Formulations may include food sources for the cultured organisms, such as barley, rice, or other biological materials such as seed, leaf, root, plant elements, sugar cane bagasse, hulls or stalks from grain processing, ground plant material or wood from building site refuse, sawdust or small fibers from recycling of paper, fabric, or wood. Other suitable formulations will be known to those skilled in the art.

In one embodiment, the agricultural formulation comprises a fertilizer. Preferably, the fertilizer is one that does not reduce the viability of the bacterial composition by more than 20%, 30%, 40%, 50% or more.

In some cases, it is advantageous for the agricultural formulation to contain agents such as herbicide, a nematicide, an insecticide, a plant growth regulator, a rodenticide, and a nutrient. Such agents are ideally compatible with the plant onto which the formulation is applied (e.g., it should not be deleterious to the growth or health of the plant). Furthermore, the agent is ideally one which does not cause safety concerns for human, animal or industrial use (e.g., no safety issues, or the compound is sufficiently labile that the commodity plant product derived from the plant contains negligible amounts of the compound).

The agricultural formulations comprising the biofilm of the present invention typically contains between about 0.1 to 95% by weight, for example, between about 1% and 90%, between about 3% and 75%, between about 5% and 60%, between about 10% and 50% in wet weight of the biofilm-incorporated beneficial bacterial population of the present invention. It is preferred that the formulation contains at least about $10^2$ CFU or spores per ml of formulation, at least about $10^3$ CFU or spores per ml of formulation, at least about $10^4$ CFU or spores per ml of formulation, at least about $10^5$ CFU or spores per ml of formulation, at least about $10^6$ CFU or spores per ml of formulation, or at least about $10^7$ CFU or spores per ml of formulation.

The present inventors also contemplate that the presently disclosed agricultural composition may be comprised in an article of manufacture which further comprises an agent which promotes the growth of plants.

The agents may be formulated together with the biofilm in a single composition, or alternatively packaged separately, but in a single container.

Suitable agents are described herein above. Other suitable agents include fertilizers, pesticides (an herbicide, a nematocide, a fungicide and/or an insecticide), a plant growth regulator, a rodenticide, and a nutrient, as further described herein below.

In one embodiment, the agent which promotes the growth of the plant lacks anti-bacterial activity.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed.

(1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Biofilm Formation

Materials and Methods

Strains and growth conditions: The probiotic bacterial strain used in this study was *Lactobacillus plantarum*. This strain routinely is grown in either MRS (Man, Rogosa & Sharpe) broth or MRS broth solidified using 1.5% agar (Difco™). The *Bacillus subtilis* wild strain NCIB3610 and its derivatives are typically cultured in LB (10 g of tryptone, 5 g of yeast extract, 5 g of NaCl per liter) broth or LB solidified with 1.5% agar. Prior to their use, *L. plantarum* and *B. subtilis* were grown on a hard agar plate for 48 h or overnight, respectively, both at 37° C. A starter culture of each strain was prepared using a single bacterial colony, *L. plantarum* inoculated into 5 mL MRS broth for 8 h without agitation and *B. subtilis* into LB medium for 5 hours at 37° C. 150 rpm, until it reached an $OD_{600}$ of approximately 1.5. For co-culture experiments, MRS medium at pH 7 was used since it was found to be effective in promoting biofilm formation by *B. subtilis* and suitable for co-culture cultivation of *B. subtilis* and probiotic lactic acid bacteria (LAB). *B. subtilis* cells were mixed with an equal amount of *L. plantarum* cells to a final concentration of $10^8$ cells/mL of each strain, and then diluted 1:100 into MRS pH 7. The cells in mixed cultures were incubated aerobically at 37° C. at 50 rpm for 7-8 h.

Mono-species biofilms of *B. subtilis* were generated in MRS (Hy-lab) medium or in MRS supplemented with LB at different ratio (1:5, 1:2, 5:1) at 30° C. In order to determine optimal conditions for *Bacillus* strains to form biofilm, the pH of MRS was gradually elevated from 6 to 8 using 1M NaOH. All strains used in this study are listed in Table 2 and are isogenic unless otherwise indicated.

TABLE 2

| Strain | Genotype |
| --- | --- |
| NCIB3610 | Undomesticated wild strain of *B. subtilis* capable of forming robust biofilms |
| RL4566 | ΔkinA::tet |
| RL4563 | ΔkinB::kan |
| RL4565 | ΔkinC::cat |
| RL4569 | ΔkinD::mls |
| RL4570 | ΔkinE::mls |
| RL4573 | ΔkinA::tet, ΔkinB::kan |
| RL4577 | ΔkinC::cat, ΔkinD::mls |
| RL4620 | Δspo0A:kan |
| RL4582 | $P_{tapA}$-lacZ at the amyE locus in 3610, Spec$^R$ |

TABLE 2-continued

| Strain | Genotype |
| --- | --- |
| YC668 | ΔabrB::kan |
| *B. paralicheniformis* MS303 | |
| *B. licheniformis* MS310 | |
| *B. licheniformis* S127 | |
| *B. subtilis* MS1577 | |
| *B. cereus* 10987 | |

Assay for colony and pellicle biofilm formation: For colony architecture analysis, 3 µL of starter cultures were spotted onto MRS agar plates or control LB and incubated at 30° C. for 72 h. For pellicle formation analysis, the starter cultures were diluted 1:100 into 3.5 mL MRS broth or control LB in a 12-well plates and incubated without agitation at 30° C. for 48 h. Images were taken using a Zeiss Stemi 2000-C microscope with an axiocam ERc 5s camera (Zeiss, Germany).

β-galactosidase assay: Cells were harvested from colonies grown in either LB, LB supplemented with MRS in different ratio (1:1, 1:5, and 5:1) or MRS with pH adjustment to 7 on solid medium at 30° C. and resuspended in phosphate-buffered saline (PBS) solution. Typical long bundled chains of cells in the biofilm colony were disrupted using mild sonication. The optical density (OD) of the cell samples were normalized to an OD600 of 1.0 in PBS. One milliliter of bacterial cell suspensions were collected and assayed according to standard procedure.

Growth curve analysis of *L. plantarum* during growth in co-culture: Overnight cultures of *B. subtilis* and *L. plantarum* were grown in LB or MRS, respectively, to the stationary phase and diluted 1:100 into 25 mL of modified MRS broth with an elevated pH (up to 7). Co-culture samples generated as described above were grown for 8 h aerobically at 37° C. and 150 rpm. *B. subtilis* and *L. plantarum* mono-species cultures were also prepared and used as control samples. Every hour, 1 mL was collected from each culture for microbial counting by colony forming units (CFU) count method. This was done by making appropriate dilutions using PBS buffer and plating them on MRS agar. The plates were incubated aerobically at 37° C. for 48 h.

Visualizing biofilm forming cells using confocal laser scanning microscopy (CLSM): *L. plantarum* cells were grown in co-culture as described above with *B. subtilis* (YC161) aborting GFP or *B. subtilis* (YC189) aborting CFP in modified MRS broth. Cell suspensions of each bacterium grown as monospecies culture served as control samples. One milliliter of each culture was collected and centrifuged at 5000 rpm for 2 minutes. After removing supernatant, the cells were washed with 1 mL of PBS buffer and then following centrifugation (at 5000 rpm for 2 minutes) resuspended in 100 µl of the same buffer. 5 µl from each sample were placed on a microscopy glass slide and visualized in a transmitted light microscope using Nomarski differential interference contrast (DIC).

Scanning electron microscopy (SEM) analysis: The cells of co-culture grown as described above were placed on glass slides coated with poly-lysine for overnight. Afterwards, glass slides were washed twice using DDW to remove unattached cells and medium remnants. The slides were exposed to 40 µl of 4% formaldehyde and incubated for 15 min at room temperature. The glass slides were washed once again using DDW and analyzed by SEM.

Analysis of survival rates following heat and cold treatment: Co-culture samples generated as described above were grown for 7-8 h aerobically at 37° C. and 50 rpm. *L. plantarum* cells grown as a monoculture were used as a control. The samples were taken to challenge tests such as heat or cold treatments. The samples were taken prior and post treatment, sonicated to break biofilm bundles (Time: 20 sec, Pulse: 10 sec, Pause: 5 sec, Amp: 30%) and conducted to CFU counting on MRS agar plates.

Analysis of *L. plantarum* survival during transition within in vitro digestion system: In order to study the survival ability of *L. plantarum* during transition in the gastrointestinal tract, samples of *L. plantarum* in mono-culture and co-culture with *B. subtilis* cells were monitored for 4 h using in vitro digestion model (Minekus et al., 2014). To simulate the gastric phase of digestion, 5 mL aliquot of suspension from each sample were mixed 1:1 with simulated gastric fluid (SGF) up to a final volume of 10 mL. Porcine pepsin (SIGMA P9700) was added to achieve 2000 U mL$^{-1}$ in the final digestion mixture, followed by CaCl$_2$ to achieve 0.075 mM in the final digestion mixture. The pH was reduced to 3.0 with 1 M HCl and the samples were placed in a water bath with a magnetic stirrer for 2 h at 37° C. Each sample was divided into 2 tubes each containing 5 mL. 50 µl of PMSF (phenylmethylsulfonyl fluoride; SIGMA P7626) was added to 1 tube to stop the reaction and then the survivability of *L. plantarum* was checked. The other tube was used in the next digestion phase—the intestinal. To simulate intestinal phase of digestion, 2.5 mL of gastric chyme was mixed 1:1 with simulated intestinal fluid (SIF) up to a final volume of 5 mL. 1 M NaOH was added to neutralize the mixture to pH 7.0 and pancreatic enzymes were added to the digestion mixture to achieve following activities in the final mixture: porcine trypsin (SIGMA T0303) (100 U mL$^{-1}$), bovin chymotrypsin (SIGMA C4129) (25 U mL$^{-1}$), porcine pancreatic a amylase (SIGMA A3176) (200 U mL$^{-1}$), porcine pancreatic lipase (SIGAM L3126) (2000 U mL$^{-1}$). In addition, bile salts (SIGMA T4009) were added to give a final concentration of 10 mM in the final mixture and then the samples were incubated again for 2.5 h. One milliliter from each sample collected after gastric and intestinal phases and the numbers of viable *L. plantarum* cells were determined using CFU counting method as described above.

Results

Development of a System for Mutual Growth of *B. subtilis* and *L. plantarum* in Co-Culture It was previously shown that biofilms have an increased tolerance toward various unfavorable environmental conditions, apparently due to production of extracellular matrix (Friedman, Kolter, & Branda, 2005). The present inventors thus hypothesized that extracellular matrix produced by robust biofilm former bacterium *B. subtilis* may provide increased protection to other species such as probiotic bacteria during their growth in co-culture biofilm system. To this end, a specialized medium was developed where *L. plantarum* and *B. subtilis* are able to grow in co-culture. It was found that by modifying the pH of the MRS to pH 7, it was possible to grow these bacteria in co-culture. As shown in FIG. 13, the co-culture cultivation had no effect on *L. plantarum* and *B. subtilis* growth (compared to their growth in pure culture), indicating that there are no antagonistic interactions between these bacteria at given conditions. Surprisingly, it was found that modification of MRS medium promotes strong biofilm formation by *B. subtilis* (FIG. 2). Since *B. subtilis* appears to be sensitive to acidic pH, the pH of MRS medium used for co-culture cultivation was gradually elevated in order to find a pH value suitable for *Bacillus* growth. The increase of pH from 6 to 8 led to a proportional increase in robustness of biofilm phenotype of both colony and pellicle biofilm (FIG. 2). When the pH was adjusted to 6 weak growth on solid MRS medium was seen and no growth in liquid medium. With pH adjustment to 6.5, not only bacterial growth in both solid and liquid MRS was observed, but surprisingly the beginning of biofilm formation on solid medium was also observed. Following an increase of pH to 7 and 8, an extremely robust biofilm phenotype in both growth setups was observed. Next, the growth rates of *B. subtilis* in MRS pH 7 and LB were compared. As can be seen in FIG. 13, a minor delay was observed at the beginning of microbial growth in MRS compare to LB. However, higher rate growth was noted later for *B. subtilis* cells grown in MRS compare to LB.

The Modified MRS Medium Promotes Biofilm Formation and Matrix Gene Expression Through KinD-Spo0A Pathway To evaluate the potential of MRS medium in promoting biofilm development and matrix genes expression, LB medium (that is usually used to culture *B. subtilis*) was enriched with different amounts of MRS (1:1, 1:5, and 5:1). Directly proportional correlation between biofilm phenotype and increase in MRS concentration was shown (FIG. 3). The effect of increasing MRS concentration on matrix gene expression in *B. subtilis* using tapA and eps operons was also investigated, since their products are major components of extracellular matrix. It was found that the expression of tapA increased proportionally with the concentration of MRS in LB (FIGS. 4A-B). The expression of eps increased proportionally to the concentration of MRS up to 80% MRS, than a decrease of expression for 100% was detected (FIGS. 5A-B).

Next, the present inventors determined whether MRS triggers biofilm formation through the Kin-Spo0A pathway previously described for *B. subtilis* (Shemesh and Chai, 2013 Journal of Bacteriology, 2013, Vol 195, No. 12 pages 2747-2754). They tested different *B. subtilis* mutants for biofilm formation (ΔkinA, ΔkinB, ΔkinC, ΔkinD, ΔkinE, ΔkinAB, ΔkinCD, Δspo0A, ΔepsΔtasA) or overproducing biofilm (ΔabrB). Firstly, they determined biofilm phenotype of mutants deficient in histidine kinases responsible for sensing environmental signals that induce biofilm formation. They found that single mutants in either kinases did not show significant defect in biofilm phenotype, although the ΔkinC and ΔkinD mutants showed a slight decrease in biofilm formation compared to control (FIG. 14). However, the ΔkinCD double mutant showed the total abolishment of biofilm phenotype (FIG. 5A). On the other hand, double mutation in ΔkinAB did not prevent biofilm formation, although some changes were observed in biofilm phenotype (in case of colony type biofilm). Mutation in master transcriptional regulator spo0A as well as double mutation in eps and tasA fully abolished biofilm formation (FIG. 5A). Mutation in the transcriptional repressor ΔabrB did not lead to an additional increase in biofilm formation compared to control WT cells (FIG. 5B). This result emphasize once again the dramatic increase in matrix production during growth of *B. subtilis* WT cells in modified MRS medium.

In order to investigate whether the biofilm-promoting effect of MRS is conserved among *Bacillus* species, other *B. subtilis* strains were tested as well as other *Bacillus* species. A biofilm promoting effect was seen as judged by wrinkled colonies (FIG. 6) and robust floating pellicles (FIG. 7).

Growth of *B. subtilis* and *L. plantarum* in Co-Culture Results in Dual Species Biofilm Development The modified MRS medium was used to investigate dual species biofilm by co-culturing fluorescently tagged *B. subtilis* cells, which constitutively express GFP (YC161), together with *L. plantarum* cells. Generated biofilm was visualized using CLSM. As can be seen in FIG. 8A (top panel), the generated biofilm consisted of both fluorescent and non-fluorescent cells. *L. plantarum* cells were surrounded by *B. subtilis* cells which attached to each other to form a biofilm-related structure (bundle). This is further illustrated in FIG. 8B which illustrates the co-cultured biofilm of *B. subtilis* and *L. plantarum* in LBGM medium.

Since biofilm formation in *B. subtilis* depends on the synthesis of extracellular matrix, the present inventors sought to determine whether the production of extracellular matrix takes place during dual species biofilm development. The level of the matrix gene expression in the formed biofilm was analyzed using transcriptional fusion of the promoter for tapA-sipW-tasA (operon responsible for synthesis of protein components of biofilm matrix in *B. subtilis*) to the cfp gene encoding cyan fluorescent protein (YC189), as described previously (Shemesh, Kolter, & Losick, 2010, J Bacteriol 192, 6352-6356) ($P_{tapA}$-cfp). Notable CFP expression was observed, indicating that the tapA-sipW-tasA operon is been activated and therefore matrix production was induced in the dual species biofilm (FIGS. 8A-B, bottom panel). To determine whether *L. plantarum* cells could be surrounded with extracellular polymeric substances derived from *B. subtilis* biofilm formation, the dual species biofilm was analyzed using SEM (FIGS. 9A-C). The obtained images (FIG. 9C) demonstrate formation of 3-dimensional and heterogeneous structure of biofilm where *L. plantarum* cells appeared to be incorporated within the extracellular matrix produced by *B. subtilis*. Importantly, *B. subtilis* cells grown as monoculture form also biofilm characterized with homogenous structure in which long filaments of the cells are bound together by an extracellular matrix (FIG. 9A). In contrast, the *L. plantarum* cells could not form notable biofilm in monospecies culture. The observations described above indicate that the extracellular matrix produced by *B. subtilis* cells could be shared with *L. plantarum* cells and thus provide them with possible protection against environmental stresses.

The Dual Species Biofilm Facilitates Survival of *L. plantarum* in Hostile Environments In order to determine whether the matrix produced by *B. subtilis* in the co-culture biofilm might provide defense to *L. plantarum* against unfavorable environment conditions, the survival of *L. plantarum* cells was tested during heat treatment (conditions that simulate industrial processing such as pasteurization) as well as during refrigerating (conditions that simulates storage conditions). For heat treatment pasteurization, *L. plantarum* cells grown in co-culture biofilm were exposed to heating at 63° C. for 1 and 3 min. For cold treatment, *L. plantarum* cells grown in co-culture biofilm were stored for up to 21 days at 4° C. *L. plantarum* cells that grew in monospecies culture were used as control. Following 1 and 3 min of heat treatment, *L. plantarum* cells grown in co-culture biofilm resulted in an increase of around 1.25 Log CFU/mL and 1.06 Log CFU/mL, respectively, in the number of viable *L. plantarum* cells, compare to control (FIGS. 10A-B). Furthermore, the results from the cold treatment experiment showed that *L. plantarum* cells grown in co-culture biofilm were much more protected throughout the storage conditions demonstrating an increase of around 0.44 to 0.89 Log CFU/mL in their viability (FIGS. 10A-B).

Extracellular Matrix Produced During Formation of Dual Species Biofilm Facilitates Survival of *L. plantarum* During Heat Treatment To further prove that increased resistance of *L. plantarum* to unfavorable environment conditions is facilitated by extracellular matrix, co-cultures of *L. plantarum* and *B. subtilis* mutant strains (either deficient in biofilm formation (ΔepsΔtasA) or an overproducing biofilm matrix (ΔabrB)) were generated. The co-cultures were subjected to heat treatment pasteurization. *L. plantarum* cells grown in mono-species culture and in co-culture with wild type *B. subtilis* were used as control. As shown in FIG. 11A, *L. plantarum* cells grown with the cells of ΔepsΔtasA double mutant did not show a significant difference in their survival level compare to *L. plantarum* grown in mono-species culture. However, a significant increase in survival of *L. plantarum* cells grown in co-culture with wild type *B. subtilis* was observed. Interestingly, an increase of about 1.78 Log CFU/mL in survival rates of the *L. plantarum* cells grown in the presence of ΔabrB mutant cells, compared to survival rates of *L. plantarum* grown in mono-culture was observed.

In another experiment, the samples were grown in milk for 18 hours at 30° C., 20 rpm. Afterwards they were heat treated at 63° C. for 1 to 3 min. Control samples were not heat treated. The number of viable *L. plantarum* cells was determined using CFU-method. *$p<0.05$. As illustrated in FIG. 11B, *B. subtilis* biofilm facilitates *L. plantarum* survival during heat in milk.

Extracellular Matrix Produced During Formation of Dual Species Biofilm Facilitates Survival of *L. plantarum* Under the Conditions Resembling the Human Digestion System In order to study the survival ability of *L. plantarum* during transition in the gastro-intestinal tract, the survival rate of *L. plantarum* cells was examined using an in vitro digestion model (FIG. 12). After 2 h of incubation in simulate gastric conditions, an increase in viable cell concentration of around 0.86 Log CFU/mL was observed for *L. plantarum* cells grown in co-culture biofilm with *B. subtilis*, compared to mono-culture *L. plantarum* cells. Afterwards, cells were incubated 2 h under simulated intestinal conditions and increase of around 0.9 Log CFU/mL in viable cell concentration was observed for *L. plantarum* cells protected by biofilm, compared to free living *L. plantarum* cells.

Example 2

Acetoin Enhances BioFilm Formation

Food products are often enriched by different food additives which may improve organoleptic and sensory characteristics of the products. Among those additives there are important small molecules such as acetoin which can improve the flavor of different food products. Acetoin is a neutral molecule which widely exists in nature. Some microorganisms, higher plants, insects, and higher animals have the ability to synthesize acetoin. Those additives can affect the physiology of many bacteria associated with human health, and affect development of multicellular community of bacterial cells known as a biofilm. Biofilm formation depends on the synthesis of an extracellular matrix that holds the constituent cells together. In *Bacillus subtilis*, a prebiotic bacteria, the matrix has two main components, an exopolysaccharide synthesized by the products of the epsA-O operon, and amyloid fibers encoded by tapA-sipW-tasA operon.

Results

As illustrated in FIGS. 15A-C, acetoin triggers the biofilm bundles formation in *Bacillus subtilis*. In the absence of acetoin, no biofilm formation is observed when grown in LB medium (FIG. 15A). FIGS. 16A-B illustrate that acetoin triggers a colony type biofilm formation in *Bacillus subtilis*. Transcription of the tapA operon responsible for the matrix production in *B. subtilis* was shown to be highly upregulated by acetoin (FIGS. 17A-D).

The results indicate that cells of *B. subtilis* develop into a complex bundle during growth in the presence of acetoin. The cells express high levels of the extracellular matrix components, in response to acetoin, which are crucial for biofilm formation.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of preparing a bacterial composition comprising:
   (a) in vitro co-culturing beneficial bacteria with biofilm-producing bacteria in a growth substrate under conditions that generate a biofilm which comprises said beneficial bacteria and said biofilm-producing bacteria; and
   (b) isolating said biofilm from said growth substrate, thereby preparing the bacterial composition.

2. The method of claim 1, wherein said biofilm-producing bacteria are non-pathogenic bacteria.

3. The method of claim 1, wherein said biofilm-producing bacteria are of the *Bacillus* genus.

4. The method of claim 3, wherein said biofilm-producing bacteria are of the *B. subtilis* species.

5. The method of claim 1, wherein said beneficial bacteria are probiotic bacteria.

6. The method of claim 5, wherein said probiotic bacteria are of the Lactobacillales order.

7. The method of claim 5, wherein said biofilm-producing bacteria are of the *B. subtilis* species.

8. The method of claim 5, wherein said probiotic bacteria are of the *L. plantarum* species.

9. The method of claim 1, wherein said beneficial bacteria are genetically modified to express a therapeutic polypeptide.

10. The method of claim 1, wherein said beneficial bacteria are used in bioremediation.

11. The method of claim 1, wherein said biofilm-producing bacteria express genes of the KinD-Spo0A pathway.

12. The method of claim 11, wherein said growth substrate is MRS.

13. The method of claim 1, wherein said growth substrate comprises a growth medium.

14. The method of claim 13, wherein said growth medium is selected from the group consisting of LB, LBGM, milk and MRS.

15. The method of claim 1, wherein when said biofilm-producing bacteria are of the *Bacillus* genus and said beneficial bacteria are of the Lactobacillales order, said growth substrate is LBGM, milk or MRS.

16. The method of claim 15, wherein said conditions comprise a pH of about 6.5-8.

17. The method of claim 16, wherein said conditions comprise a pH of 6.8-7.5.

18. The method of claim 1 wherein said growth substrate comprises acetoin.

19. The method of claim 1, further comprising dehydrating said biofilm following said isolating.

20. The method of claim 1, wherein said beneficial bacteria comprise no more than 50 bacterial species.

21. The method of claim 1, wherein said biofilm-producing bacteria are a single species of biofilm-producing bacteria.

* * * * *